United States Patent
Krueger et al.

(10) Patent No.: US 12,162,013 B2
(45) Date of Patent: Dec. 10, 2024

(54) CELL SORTER WITH PIVOTAL SCUPPERS

(71) Applicant: CYTEK BIOSCIENCES, INC., Fremont, CA (US)

(72) Inventors: Glen Krueger, Fremont, CA (US); David Vrane, Fremont, CA (US); Kuncheng Wang, Fremont, CA (US); Qiuta Gu, Fremont, CA (US)

(73) Assignee: Cytek Biosciences, Inc., Fremont, CA (US)

( * ) Notice: Subject to any disclaimer, the term of this patent is extended or adjusted under 35 U.S.C. 154(b) by 24 days.

(21) Appl. No.: 17/829,321

(22) Filed: May 31, 2022

(65) Prior Publication Data

US 2022/0371017 A1 Nov. 24, 2022

Related U.S. Application Data

(63) Continuation of application No. 17/665,482, filed on Feb. 4, 2022.
(Continued)

(51) Int. Cl.
*B01L 3/00* (2006.01)
*C12M 1/00* (2006.01)
(Continued)

(52) U.S. Cl.
CPC ... *B01L 3/502761* (2013.01); *B01L 3/502715* (2013.01); *C12M 47/04* (2013.01);
(Continued)

(58) Field of Classification Search
CPC ......... B01L 3/502761; B01L 3/502715; B01L 2300/0663; B01L 2300/0681;
(Continued)

(56) References Cited

U.S. PATENT DOCUMENTS 5,030,002 A 7/1991 North, Jr.
10,866,182 B2 12/2020 Marks et al.
(Continued)

OTHER PUBLICATIONS

Thomas, Shane; "International Search Report" and "Written Opinion"; PCT/US2022/070543; une 29, 2022; 12 pages.
(Continued)

*Primary Examiner* — Jill A Warden
*Assistant Examiner* — Alex Ramirez
(74) *Attorney, Agent, or Firm* — Alford Law Group, Inc.

(57) ABSTRACT

A compact sorting flow cytometer system is disclosed. The system includes a flow cell and a deflection unit in communication with the flow cell to receive charged drops and uncharged drops in a stream of a sample biological fluid. The deflection unit includes a case having a deflection cone and chamber, a tub with a drain, and a slot in a base. The deflection unit further includes electrostatic charge plates in the cone forming an electrostatic charge field; and first and second pivotal scuppers, and a center non-pivotal collector arranged along a shaft in the tub of the case. Uncharged drops pass the electrostatic charge field undeflected in a center stream path while charged drops are deflected away from it. The pivotal scuppers pivot between positions to direct charged drops into the tub for aspiration or to pass through the slot in the base for collection.

9 Claims, 28 Drawing Sheets

Related U.S. Application Data

(60) Provisional application No. 63/172,330, filed on Apr. 8, 2021, provisional application No. 63/258,065, filed on Apr. 8, 2021, provisional application No. 63/172,072, filed on Apr. 7, 2021, provisional application No. 63/146,562, filed on Feb. 5, 2021.

(51) Int. Cl.
| | | |
|---|---|---|
| *G01N 15/01* | (2024.01) | |
| *G01N 15/10* | (2024.01) | |
| *G01N 15/14* | (2024.01) | |
| *G01N 15/1409* | (2024.01) | |
| *G01N 15/1434* | (2024.01) | |
| *G01N 15/149* | (2024.01) | |

(52) U.S. Cl.
CPC ......... *G01N 15/14* (2013.01); *G01N 15/1436* (2013.01); *B01L 2300/0654* (2013.01); *B01L 2300/0663* (2013.01); *B01L 2300/0681* (2013.01); *B01L 2300/0829* (2013.01); *B01L 2300/1805* (2013.01); *B01L 2300/1894* (2013.01); *G01N 15/01* (2024.01); *G01N 2015/1006* (2013.01); *G01N 2015/1028* (2024.01); *G01N 15/1409* (2024.01); *G01N 15/149* (2024.01)

(58) Field of Classification Search
CPC ..... B01L 2300/0829; B01L 2300/1805; B01L 2300/1894; C12M 47/04; G01M 15/14; G01N 2015/0065; G01N 2015/1006; G01N 2015/1409; G01N 2015/149; G01N 15/14; G01N 15/0065; G01N 15/1409; G01N 15/149

See application file for complete search history.

(56) References Cited

U.S. PATENT DOCUMENTS

| | | |
|---|---|---|
| 2001/0003380 A1 | 6/2001 | Albinsson |
| 2004/0062685 A1 | 4/2004 | Norton et al. |
| 2005/0019949 A1 | 1/2005 | Hall et al. |
| 2007/0003434 A1 | 1/2007 | Padmanabhan et al. |
| 2009/0107893 A1* | 4/2009 | Schembri ........... G01N 15/1459 209/127.1 |
| 2012/0103112 A1 | 5/2012 | Vrane et al. |
| 2013/0105113 A1 | 5/2013 | Dolgonos |
| 2014/0211205 A1 | 7/2014 | Bardell et al. |
| 2018/0156710 A1 | 6/2018 | Vrane et al. |
| 2018/0156711 A1 | 6/2018 | Vrane |

OTHER PUBLICATIONS

Picto, Julien, et al.; "Flow cytometry: retrospective, fundamentals and recent instrumentation"; Cytotechnology, vol. 64, pp. 109-130, Springer Science+Business Media B.V.; Jan. 21, 2012; 22 pages total.

\* cited by examiner

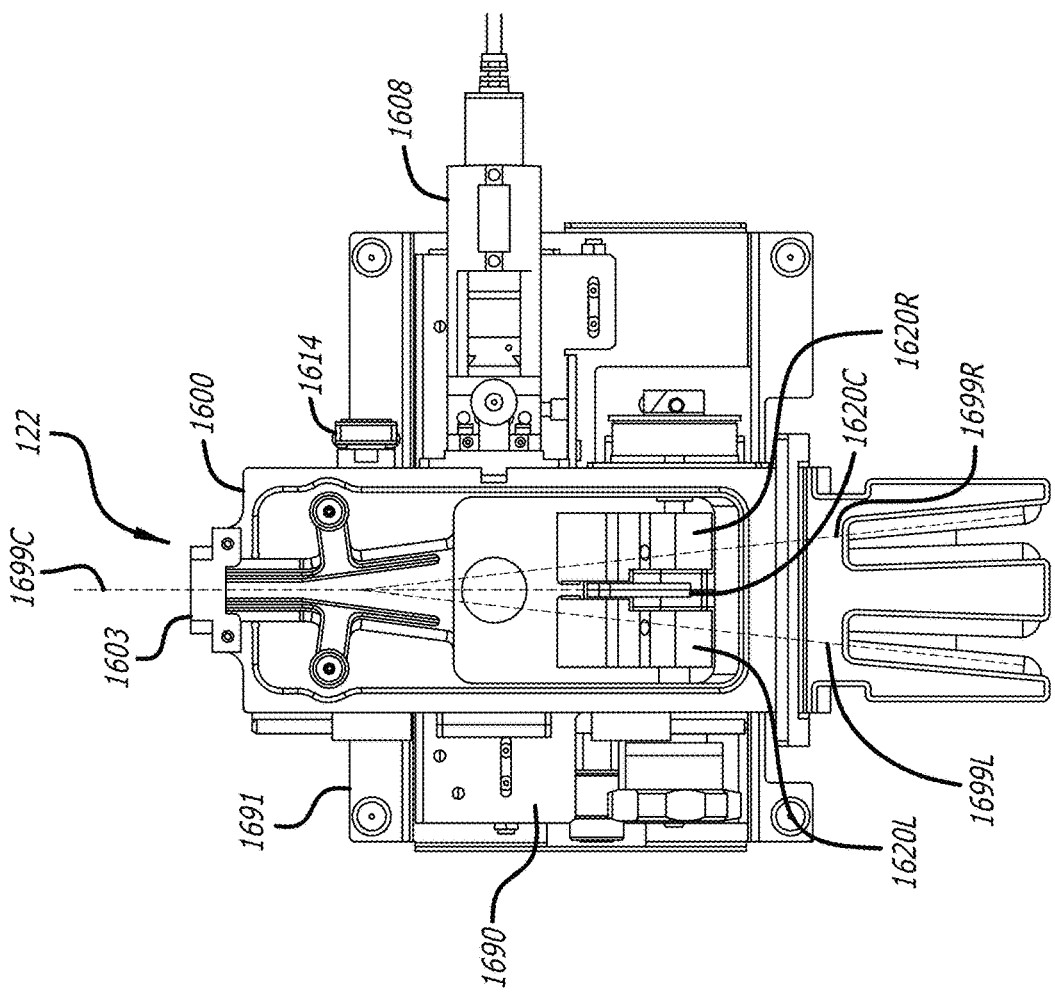
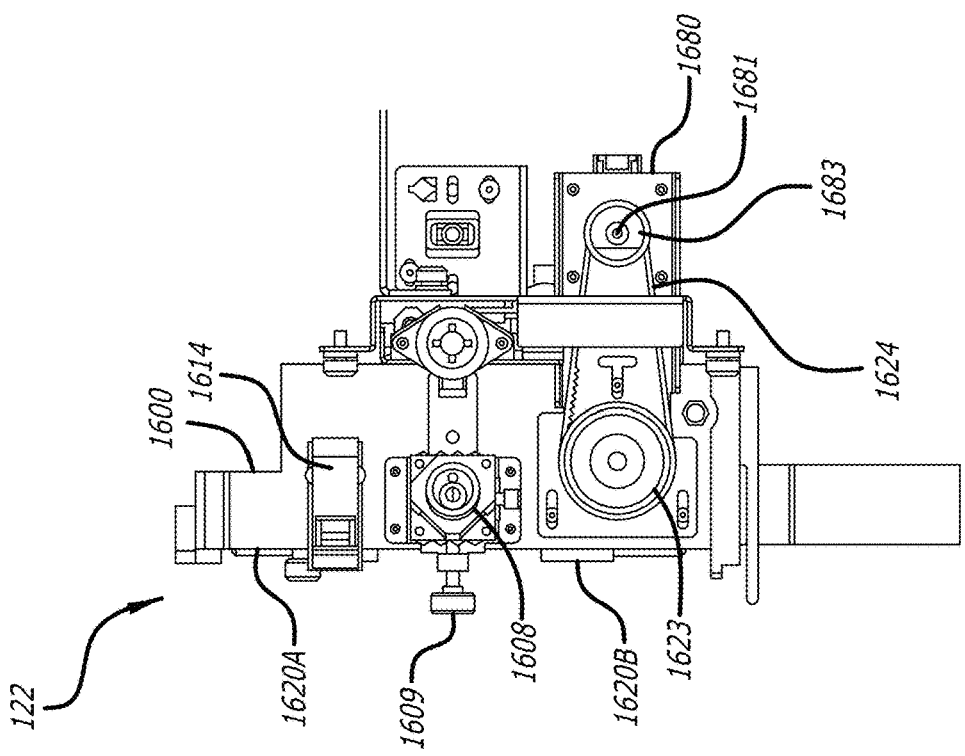
FIG. 5F
FIG. 5E

CELL SORTER WITH PIVOTAL SCUPPERS

CROSS-REFERENCE TO RELATED APPLICATIONS

This patent application is a continuation and claims the benefit of United States (U.S.) Non-Provisional patent application Ser. No. 17/665,482 titled INTEGRATED AIR FILTERING AND CONDITIONING OF DROPLET CHAMBER IN A COMPACT CELL SORTER filed on Feb. 4, 2022 by inventors Glen Krueger et al. U.S. Non-Provisional patent application Ser. No. 17/665,482 claims the benefit of United States (U.S.) Provisional Patent Application No. 63/172,330 titled INTEGRATED AIR FILTERING AND CONDITIONING OF DROPLET CHAMBER IN A COMPACT CELL SORTER filed on Apr. 8, 2021 by inventors Glen Krueger et al., incorporated herein by reference for all intents and purposes. U.S. Non-Provisional patent application Ser. No. 17/665,482 claims the benefit of United States (U.S.) Provisional Patent Application No. 63/258,065 titled INTEGRATED AIR FILTERING AND CONDITIONING OF DROPLET CHAMBER IN A COMPACT CELL SORTER filed on Apr. 7, 2021 by inventors Glen Krueger et al., incorporated herein by reference for all intents and purposes. U.S. Non-Provisional patent application Ser. No. 17/665,482 claims the benefit of United States (U.S.) Provisional Patent Application No. 63/172,072 titled INTEGRATED COMPACT CELL SORTER filed on Apr. 7, 2021 by inventors Glen Krueger et al., incorporated herein by reference for all intents and purposes. U.S. Non-Provisional patent application Ser. No. 17/665,482 claims the benefit of United States (U.S.) Provisional Patent Application No. 63/146,562 titled LOADING SYSTEM WITH MAGNETICALLY COUPLED SAMPLE MOVER FOR FLOW CYTOMETRY AND CELL SORTER SYSTEMS filed on Feb. 5, 2021 by inventors Babak Honaryar et al., incorporated herein by reference for all intents and purposes.

FIELD

The embodiments of the invention relate generally to cell sorter systems.

BACKGROUND

Flow cytometry and cell sorting involves the optical measurement of cells or particles of a test sample carried in a fluid flow. Cell sorting further sorts out the cells of interest into different test containers (e.g., test tubes) for further usage (e.g., testing) or counting. The lab instruments that achieve these tasks are known as a flow cytometer and a cell sorter, also referred to as a sorting flow cytometer.

Oftentimes external supporting equipment is connected to a flow cytometer or cell sorter to safely operate them to be sure dangerous molecules or biological cells are not released into a lab. In other cases, temperature of molecules or biological cells under test needs to be maintained within a range. External supporting equipment is often connected to a flow cytometer or cell sorter to maintain an acceptable temperature range that does not damage the molecules or cells. However, the external supporting equipment comes at extra costs, including monetary, taking up space in a lab that could be used for other lab equipment or additional flow cytometers or cell sorters.

It is desirable to reduce the footprint of the flow cytometer/cell sorter so more can be placed in a lab and on desktops. Accordingly, a more compact integrated flow cytometer and cell sorter is desirable to improve upon prior systems.

BRIEF SUMMARY

The embodiments are summarized by the claims.

BRIEF DESCRIPTIONS OF THE DRAWINGS

Various embodiments are illustrated by way of example, and not by way of limitation, in the Figures of the accompanying drawings.

FIG. 5E is a right side view of the deflection unit, with covered removed, of the sorting system of the compact cell sorter system.

FIG. 5F is a front view of the deflection unit, with covered removed, of the sorting system of the compact cell sorter system.

It will be recognized that some or all of the Figures are for purposes of illustration and do not necessarily depict the actual relative sizes or locations of the elements shown. The Figures are provided for the purpose of illustrating one or more embodiments with the explicit understanding that they will not be used to limit the scope or the meaning of the claims.

DETAILED DESCRIPTION

In the following detailed description of the embodiments, numerous specific details are set forth. However, it will be obvious to one skilled in the art that the embodiments may be practiced without these specific details. In other instances, well known methods, procedures, components, and circuits have not been described in detail so as not to unnecessarily obscure aspects of the embodiments. The various sections of this description are provided for organizational purposes. However, many details and advantages apply across multiple sections.

Sorter System Overview

Figure 1A:
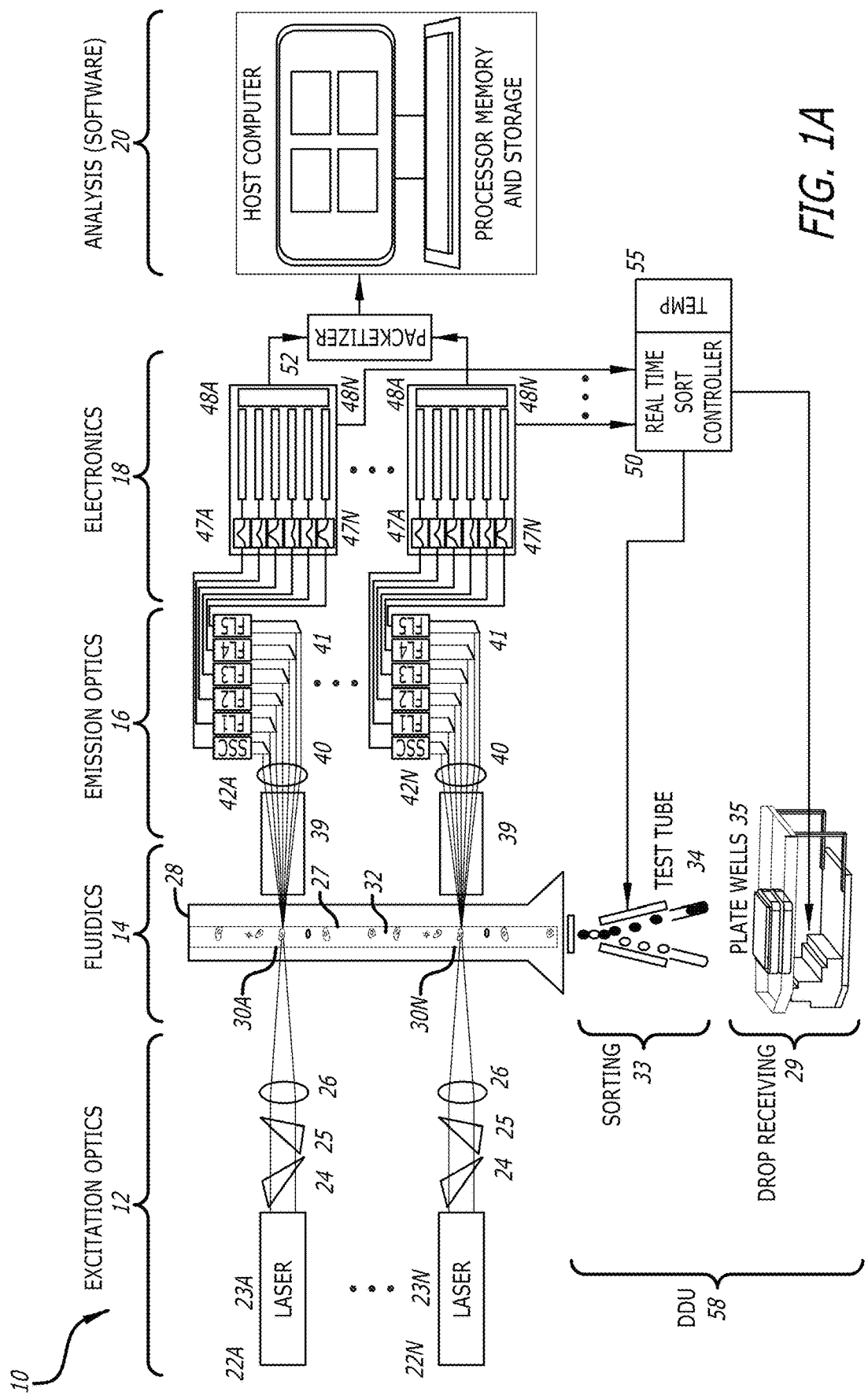
FIG. 1A is a basic conceptual diagram of a cell sorter system (a sorting flow cytometer system) and a flow cytometer system is shown.

FIG. 1A is a basic conceptual diagram of a compact cell sorter system (compact sorting flow cytometer system) 10. Five major subsystems of the system 10 include an excitation optics system 12, a fluidics system 14, an emission optics system 16, an acquisition system 18, and an analysis system 20. The fluidics system 14 can include a sample loading system (see sample input station 130 shown in FIG. 1C), an interrogating system 28, a cell sorting system 33, and a droplet deposition (droplet receiving) system 29. Generally, a "system" and "subsystem" includes (electrical, mechanical, and electro-mechanical) hardware devices, software devices, or a combination thereof.

The excitation optics system 12 includes, for example, a plurality (e.g., two to five) of excitation channels 22A-22N each having a different laser device 23A-23N and one or more optical elements 24-26 to direct the different laser light to optical interrogation regions 30A-30N spaced apart along a line in a flow channel 27 of a flow cell 28. Example optical elements of the one or more one or more optical elements 24-26 include an optical prism and an optical lens. The excitation optics system 12 illuminates an optical interrogation region 30 in a flow cell 28. The fluidics system 14 carries a fluid sample 32 surrounded by a sheath fluid through each of a plurality of optical interrogation regions 30A-30N in the flow cell/flow channel.

The emission optics system 16 includes a plurality of detector arrays 42A-42N each of which, for example, includes one or more optical elements 40, such as an optical fiber and one or more lenses to direct fluorescent light and/or (forward, side, back) scattered light to various electro-optical detectors (transducers), including a side scatter (SSC) channel detector and a plurality (e.g., 16, 32, 48, 64) of fluorescent wavelength range optical detectors in each array, such as a first fluorescent optical detector (FL1) receiving a first wavelength range of fluorescent light, a second fluorescent optical detector (FL2) receiving a second wavelength range of fluorescent light, a third fluorescent optical detector (FL3) receiving a third wavelength range of fluorescent light, a fourth fluorescent optical detector (FL4) receiving a fourth wavelength range of fluorescent light, a fifth fluorescent optical detector (FL5) receiving a fifth wavelength range of fluorescent light, and so on to an Nth fluorescent optical detector (FLN) receiving an Nth wavelength range of fluorescent light. Each of the detector arrays 42A-42N receives light corresponding to the cells/particles that are struck and/or one or more fluorescent dyes that attached thereto and excited by the differing laser light in interrogation regions/points 30A-30N along the flow channel 27 of the flow cell 28 by each of the corresponding plurality of lasers 23A-23N. The emission optics system 16 gathers photons emitted or scattered from passing cells/particles and/or a fluorescent dyes attached to the cells/particles. The emission optics system 16 directs and focuses these collected photons onto the electro-optical detectors SSC, FL1, FL2, FL3, FL4, and FL5 in each detector array, such as by fiber optic (optical fibre) cables 39, one or more one or more lenses 40, and one or more mirrors/filters 41. Electro-optical detector SSC is a side scatter channel detector detecting light that scatters off the cell/particle. The electro-optical detectors FL1, FL2, FL3, FL4, and FL5 are fluorescent detectors may include band-pass, or long-pass, filters to detect a particular and differing fluorescence wavelength ranges from the different fluorescent dyes excited by the different lasers. Each electro-optical detector converts photons into electrical pulses and sends the electrical pulses to the acquisition (electronics) system 18.

For each detector array 42A-42N, the acquisition (electronics) system 18 includes one or more analog to digital converters 47A-47N and one or more digital storage devices 48A-48N that can provide a plurality of detector channels (e.g., 16, 32, 48 or 64 channels) of spectral data signals. The spectral data signals can be signal processed (e.g., digitized by the A/Ds) and time stamped, and packeted together by a packetizer 52 into a data packet corresponding to each cell/particle in the sample). These data packets for each cell/particle can be sent by the acquisition (electronics) system 18 to the analysis system 20 for further signal processing (e.g., converted/transformed from time domain to wavelength domain) and overall analysis. Alternatively, or conjunctively, time stamped digital spectral data signals from each channel that is detected can be directly sent to the analysis system 20 for signal processing.

The analysis system 20 includes a processor, memory, and data storage to store the data packets of time stamped digital spectral data associated with the detected cells/particles in the sample. The analysis system 20 further includes software with instructions executed by the processor to convert/transform data from the time domain to data in a wavelength/frequency domain and stich/merge data together to provide an overall spectrum for the cell/particle/dyes excited by the different lasers and sensed by the detector arrays. With detection of the type of cell/particle through the one or more fluorescent dyes attached thereto, a count of the cells/particles can be made in a sample processed by a flow cytometer and/or cell sorter.

In some cases, it is desirable to sort out the cells in a sample for further analysis with a cell sorter (sorting flow cytometer). Accordingly, the spectral data signals can also be processed by a real time sort controller 50 in the acquisition (electronics) system 18 and used to control a sorting system 33 to sort cells or particles into one or more test tubes 34. In which case, the sorting system 33 is in communication with the real time sort controller 50 of the acquisition (electronics) system 18 to receive control signals. Instead of test tubes 34, the spectral data signals can also be processed by the real time sort controller 50 of the acquisition (electronics) system 18 and used to control both the sorting system 33 and a droplet deposition system 29 to sort cells or particles into wells 35 of a moving capture tray/plate. In which case, both the droplet deposition system 29 and the sorting system 33 are in communication with the acquisition (electronics) system 18 to receive control signals. In an alternate embodiment, the analysis system 20 can generate these control signals from analyzing the spectral data signals in order to sort out different cells/molecules and control the sorting system 33 and the droplet deposition system 29 to capture the drops of samples with cells/particles into one or more wells 35 of the plurality of wells in the capture tray/plate.

U.S. patent application Ser. No. 15/817,277 titled FLOW CYTOMETERY SYSTEM WITH STEPPER FLOW CONTROL VALVE filed by David Vrane on Nov. 19, 2017, now issued as U.S. Pat. No. 10,871,438; U.S. patent application Ser. No. 15/659,610 titled COMPACT DETECTION MODULE FOR FLOW CYTOMETERS filed by Ming Yan et al. on Jul. 25, 2017; and U.S. patent application Ser. No. 15/942,430 COMPACT MULTI-COLOR FLOW CYTOMETER HAVING COMPACT DETECTION MODULE filed by Ming Yan et al. on Mar. 30, 2018, each of which disclose exemplary flow cytometer systems and subsystems all which are incorporated herein by reference for all intents and purposes. U.S. Pat. No. 9,934,511 titled Rapid Single Cell Based Parallel Biological Cell Sorter issued to Wenbin Jiang on Jun. 19, 2016, discloses a cell sorter system that is incorporated herein by reference for all intents and purposes.

Compact Cell Sorter

Figure 1B:
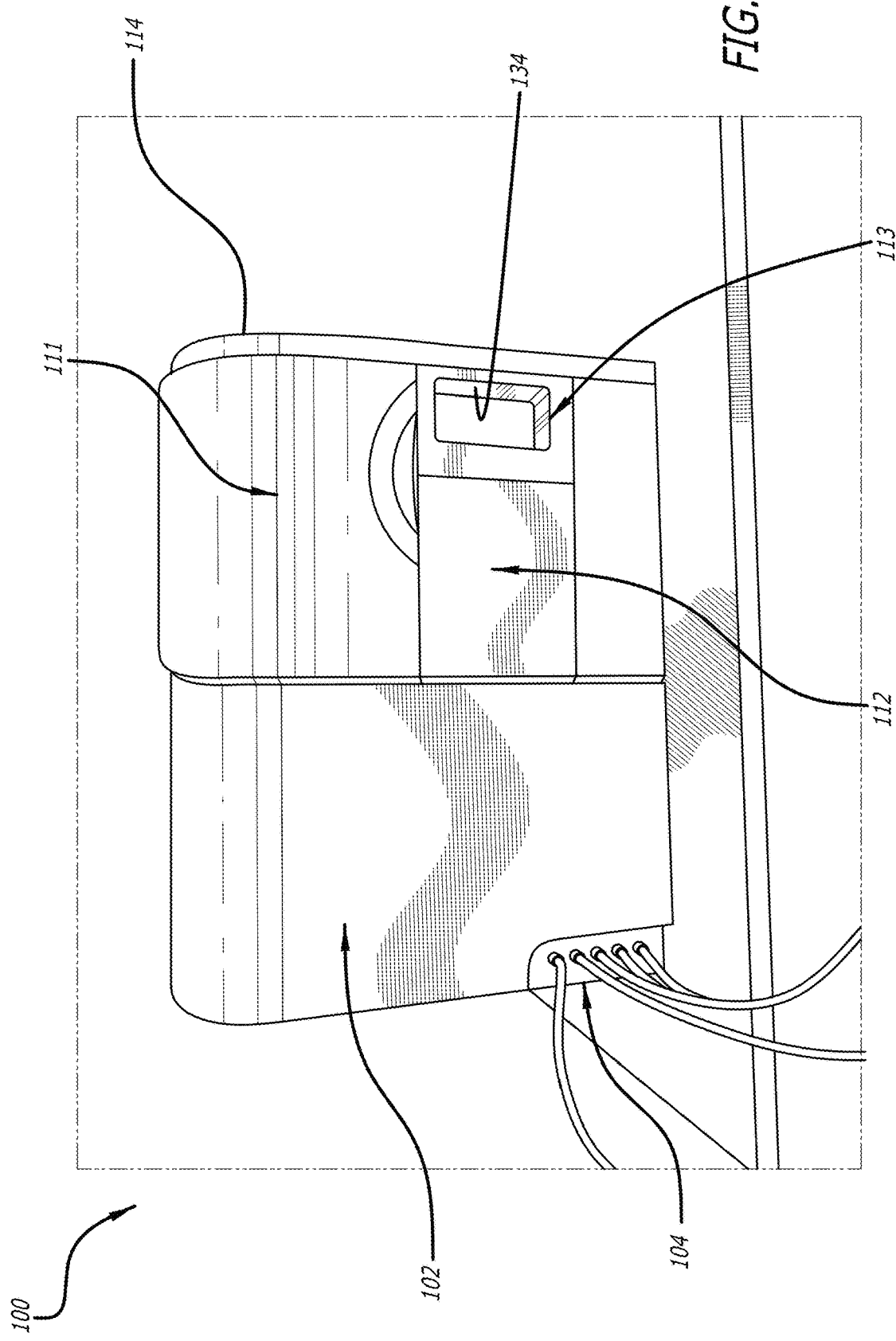
FIG. 1B is front view of a compact cell sorter system with its various doors in a closed state.

FIG. 1B illustrates a front view of an integrated compact cell sorter system (integrated compact sorting flow cytometer system) 100. The integrated compact cell sorter system 100 includes a chassis/frame 101 (see FIG. 1C) to support the various systems and subsystems of the cell sorter. A fluidics panel/door 102, a flow cell door 111, a droplet deposition unit (DDU) door 112, and a sample input door 113 are pivotally coupled to the chassis/frame 101 to cover over and seal various chambers of the cell sorter system. One or more side panels 114 are used to cover over other portions of the chassis/frame and the subsystems therein in a more fixed manner. A fluidics input/output panel 104 connects the cell sorter system 100 to external fluid tanks and an external gas supply, such as a pressurized air supply.

Figure 1C:
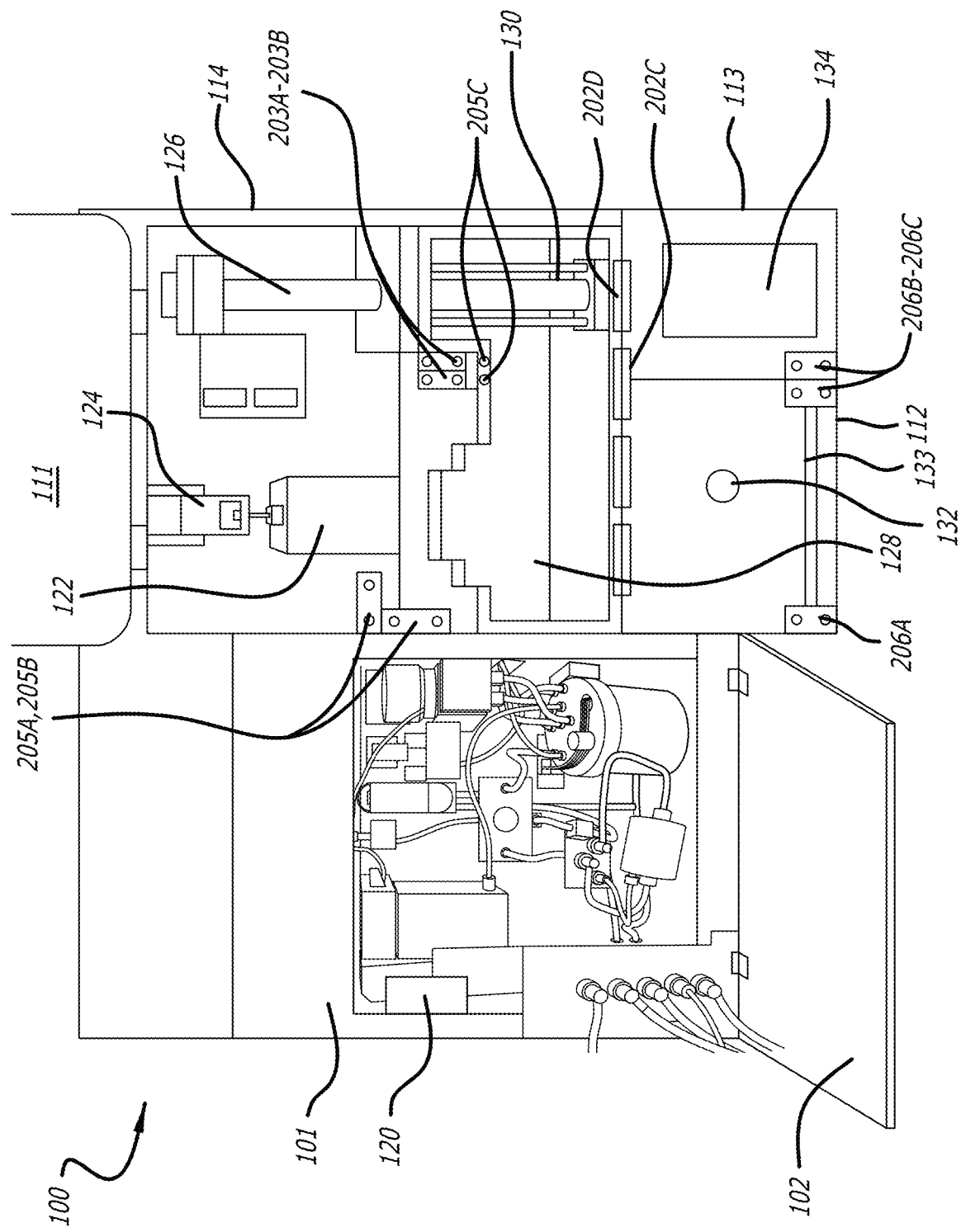
FIG. 1C is front view of a compact cell sorter system with its various doors in an open state.

Referring now to FIG. 1C, a front view of the integrated complex cell sorter system 100 is shown with opened doors and panels removed. The fluidics panel/door 102, the flow cell door 111, the DDU door 112, and the sample input door 113 of the integrated compact cell sorter system 100 are pivoted to an open position around hinges to reveal the various systems and subsystems of the cell sorter system. The integrated compact cell sorter system 100 includes a fluidics bucket 120, a deflection chamber (unit) 122, a flow cell 124, a sample pressure chamber 126, a droplet deposition unit (DDU) chamber or collection chamber 128, a sample input station (SIS) 130, and a sort collection camera 132. The sample input door 113 has a window 134 through which a sample tube can be viewed if mounted in the SIS 130. The DDU door 112 has a sort collection camera 132 that can view left and right deflected drops fall out of a slot in the deflection chamber 122 and into the DDU chamber 128 to be collected by test tubes or wells in a well plate.

The fluidics bucket 120 (part of the fluidics system 1800 of FIG. 18) includes a gas bubble remover eliminating gas bubbles in the sheath fluid. The fluidics bucket 120 is further discussed with reference to FIGS. 3A-3B. The fluidics system is under pressure to cause a sheath fluid and a sample biological fluid to flow.

The flow cell 124 is coupled in communication with the fluidics bucket 120 to receive the sheath fluid. A sample biological fluid flows with cells or particles through the flow cell 124 to be surrounded by the sheath fluid. The flow cell 124 is further discussed with reference to FIGS. 4A-4B.

The deflection chamber 122 is under the flow cell 124 to receive the drops of sample biological fluid and sheath fluid out of the flow cell 124. The deflection chamber 122 to deflects one or more of charged drops away from the center stream path 1699C along one or more deflection paths (e.g., 1699L,1699R). The deflection chamber 122 is further discussed with reference to FIGS. 5A-5L and 10B.

The droplet deposition unit (DDU) chamber/system 128 is in communication with the deflection chamber 122 to receive selectively deflected drops in the stream of the sample biological fluid with the one or more biological cells or particles into one or more containers. The DDU chamber 128 is further discussed with reference to FIGS. 10, 2A-2B, and 7A-10B.

In one embodiment, the flow cell 124 includes a flow cell body coupled in communication with the fluidics system to receive the sheath fluid, the flow cell body having charging port to charge the droplets, the flow cell body having a chamber with a circular cylindrical portion and a funnel portion, the funnel portion to form a fluid stream of the sample fluid surrounded by the sheath fluid out of a bottom side opening; a drop drive assembly coupled to the flow cell body, the drop drive assembly including a glass sample injection tube (SIT) inserted into the chamber of the flow cell body and having a first end located in the funnel portion of the chamber, the glass sample injection tube having a second end coupled in communication with the fluidics system to receive the sample fluid and inject the sample fluid into the funnel portion of the chamber; and a cuvette coupled to a base of the flow cell body, the cuvette having a flow channel adjacent the bottom side opening of the flow cell body, the cuvette to receive the fluid stream of the sample fluid surrounded by the sheath fluid out of the bottom side opening, the cuvette being transparent to light and allowing the sample fluid to undergo interrogation in the flow channel by a plurality of different lasers to determine a plurality of different types of cells or particles in the sample fluid.

In one embodiment, the flow cell 124 includes a flow cell body coupled around the drop drive assembly to receive the sample fluid from the sample injection tube, the flow cell body coupled in communication with the fluidics system to receive the sheath fluid, the flow cell body having a charging port to charge the droplets, the flow cell body having a funnel portion to form a fluid stream of the sample fluid surrounded by the sheath fluid out of an opening; and a cuvette coupled to a base of the flow cell body, the cuvette having a channel to receive the fluid stream of the sample fluid surrounded by the sheath fluid out of the opening, the cuvette being transparent to light and allowing the sample fluid to undergo interrogation in the channel by a plurality of different lasers to determine a plurality of different types of cells or particles therein.

In one embodiment, the flow cell 124 further includes a nozzle assembly selectively engaged with the cuvette, the nozzle assembly having a nozzle and an O-ring around the nozzle selectively pressed against a face of the cuvette around the channel, the nozzle receiving the sample stream from the cuvette and forming sample drops out of the nozzle assembly; a carriage assembly slidingly coupled to the flow cell body, the carriage assembly to slidingly receive the nozzle assembly; and a linkage pivotally coupled to the carriage assembly and the flow cell body, the linkage including a lever arm to selectively engage the nozzle with the cuvette to receive a fluid stream and selectively disengage the nozzle from the cuvette to repair or replace the nozzle.

In one embodiment, the flow cell 124 further includes a lever hinge formed to be statically coupled to the flow cell body; a carriage release lever rotatably coupled to the lever hinge; and two lever arms rotatably coupled to the carriage release lever and to a carriage plate of the carriage assembly, wherein the two lever arms, the carriage plate, the carriage release lever, and the lever hinge have a kinematic linkage that enables the carriage assembly to maintain a vertical movement along the center axis.

In one embodiment, the flow cell 124 further includes a nozzle assembly having a nozzle handle having a body with a gripping end and a nozzle end, the body having a through hole between top and bottom surfaces near the nozzle end with a partial gland in the top surface extending around the through hole, the partial gland having a slot extending out from the through hole to the nozzle end of the nozzle handle; a nozzle insert positioned in a portion of the through hole of the body of the nozzle handle, the nozzle insert having a circular body with a center nozzle orifice concentric with the through hole to flow drops of a sample fluid, and a beveled ring in a top surface extending out from the circular body; a gasket positioned in the partial gland against the beveled ring of the nozzle insert with a portion extending above the top surface of the nozzle insert and the top surface of the nozzle handle, the gasket to provide a seal around the center nozzle orifice; and wherein the slot extending out from the partial gland to the nozzle end facilitates removal of the gasket.

In one embodiment, the DDU system 128 includes a case or a housing with an open face surround by edges of the case, the case forming a portion of a containment chamber, the case having a top side opening aligned with the deflection chamber to receive the selectively deflected drops in the stream of the sample biological fluid into one or more containers in the containment chamber, a seal mounted around edges of the case, one or more hinges coupled to a bottom portion of the case, and a door coupled to the one or more hinges to pivot the door about the one or more hinges, the door when closed to press against the seal and close off the containment chamber from an external environment.

In one embodiment, the DDU system 128 includes an electromagnetic lock comprising at least one electromagnet mounted to the case and a metal latch coupled to an inside surface of the door, wherein the metal latch is attracted to the at least one electromagnet when the door is closed and the at least one electromagnet is energized.

In one embodiment, the DDU system 128 includes a magnetic lock comprising at least one magnet mounted to the case and a metal latch coupled to an inside surface of the door, wherein the metal latch is attracted to the at least one magnet when the door is closed.

DDU Chamber

Figure 2A:
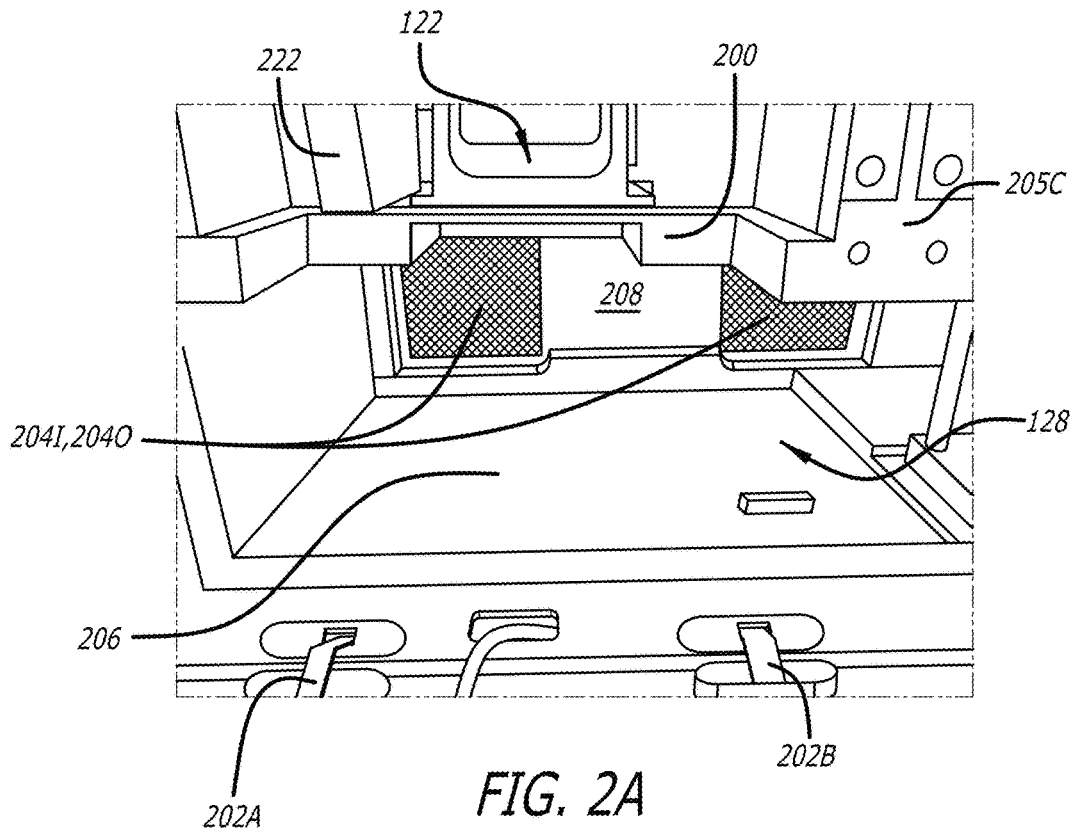
FIGS. 2A-2B are views of the droplet deposition unit (DDU) of the compact cell sorter system with the DDU door and the sample input door open.

FIG. 2A illustrates a portion of the deflection chamber 122 with its door 222 being open. The DDU chamber 128 of the cell sorter 100 is viewable with both the doors 112-113 pivoted to open positions. Openings in a wall 208 of the DDU chamber 128 show an input air filter 204I and an output air filter 204O mounted within tunnels leading to an air conditioning chamber. Behind the wall 208 are one or more fans and at least one heating/air conditioning element to force the air through the air filters and maintain a desirable range of temperatures of the sample in the SIS 130 and the sorted cells/molecules in the chamber 128.

At a base of the DDU chamber 128 is a separation plate 206 that separates a driver mechanism under the separation plate from the DDU chamber 128. Under the separation plate 206 are magnetic control mechanisms to control movement of a magnetically coupled puck 210 shown in FIG. 2B. A magnetic loading system for the DDU chamber and the magnetically coupled puck 210 is disclosed by U.S. provisional patent application No. 63/146,562, titled LOADING SYSTEM WITH MAGNETICALLY COUPLED SAMPLE MOVER FOR FLOW CYTOMETRY AND CELL SORTER SYSTEMS filed on Feb. 5, 2021 by Babak Honaryar et al. and incorporated herein by reference for all intents and purposes. Movement of the magnetically coupled puck 210 is controlled underneath the separation plate 206 by the magnetic loading system.

Figure 2B:
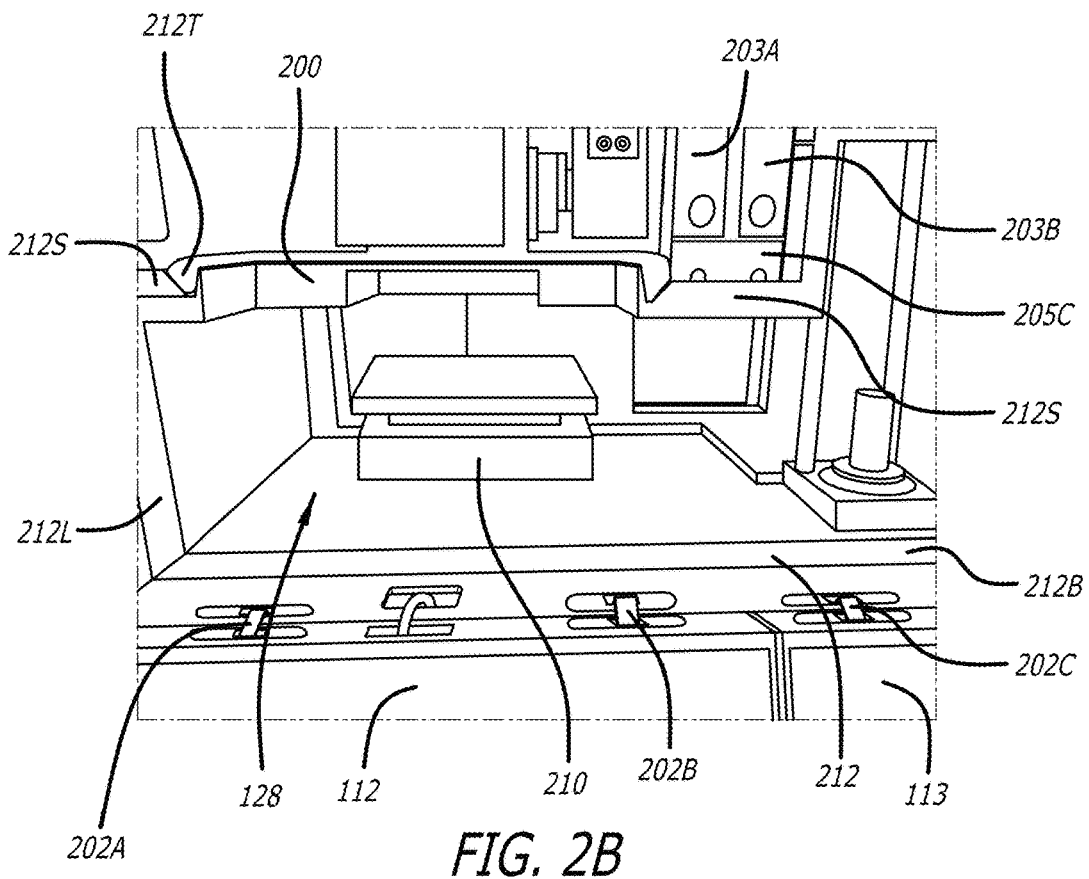

FIG. 2B illustrates a seal 212 that is mounted along edges of the DDU chamber 128 and the sample input station 130 to provide air resistive seal when the DDU door 112 and sample door 113 are closed. The DDU door 112 has a shelf 133 (shown in FIG. 1C) that presses down on a top seal portion 212T when closed. Other portions of the seal 212, such as the bottom portion 212B and side portions 212S, 212L, are pushed on by the doors 112-113 and squeezed up against the edges of the DDU chamber 128. With the doors closed, the DDU chamber 128 is sealed off from the ambient air of the environment (e.g., laboratory) where the cell sorter 100 is stationed. Furthermore, the DDU chamber 128 and SIS 130 are under negative pressure from a vacuum to additionally help prevent cells/molecules/gases from escaping out of the cell sorter into the ambient air of the environment, such as a laboratory.

The DDU door 112 and sample input door 113 provide a good seal to isolate the DDU chamber 128 from other parts of the flow cytometer/cell sorter 100 as well as the ambient environment. The sample drops sorted out and captured in the DDU chamber 128 may desire a temperature-controlled environment to maintain them. Furthermore, the cells that are captured may be a pathogen that are not desired to be an aerosol and escape into the environment. Accordingly, with the magnetic loading system and the sealed doors, the cell sorter can provide an integrated filtration system and temperature-controlled environment to the DDU chamber 128.

Fluidics Bucket

Figure 3A:
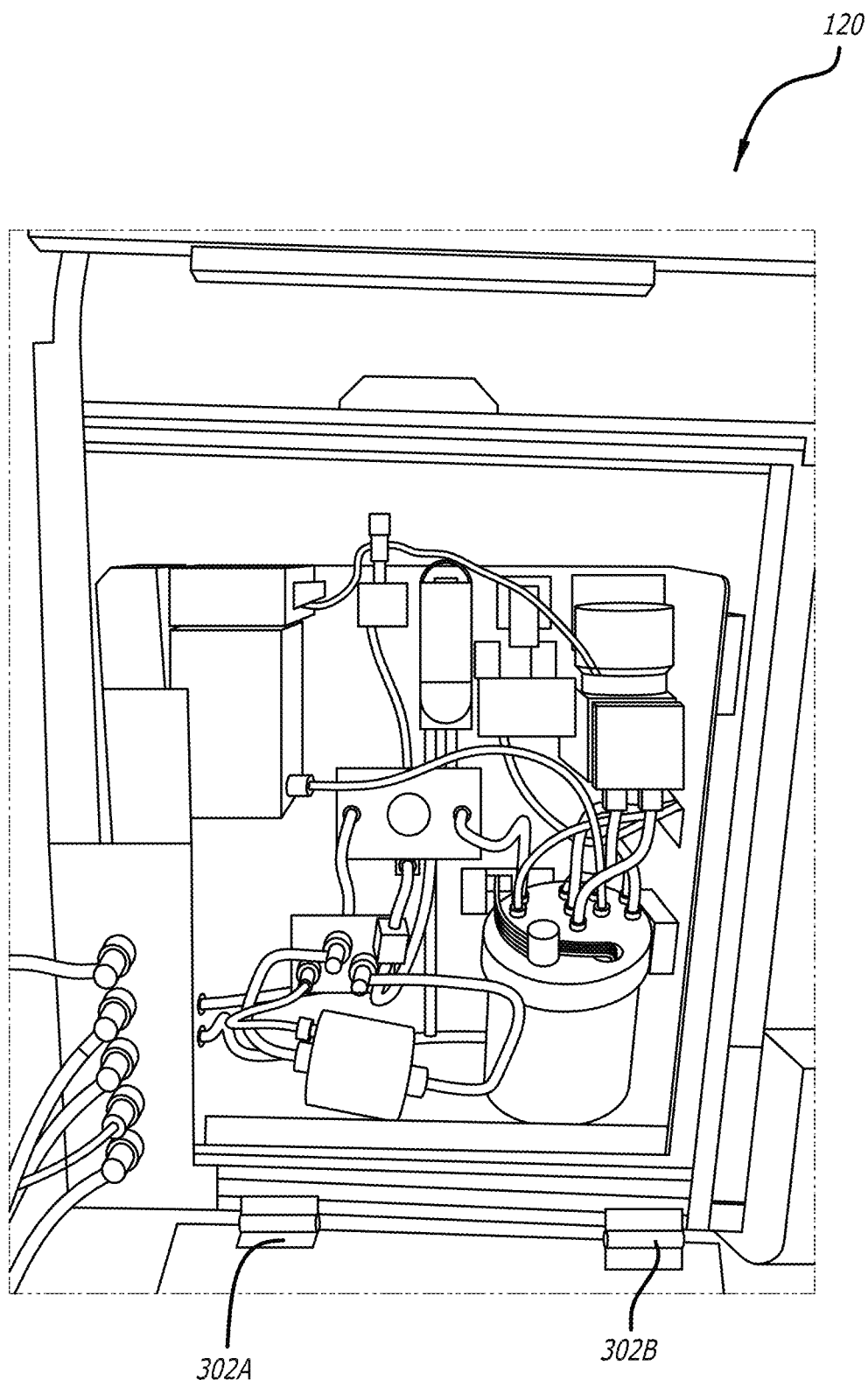
FIGS. 3A-3B are views of the fluidics bucket in the fluidics system of the compact cell sorter system.
Figure 3B:
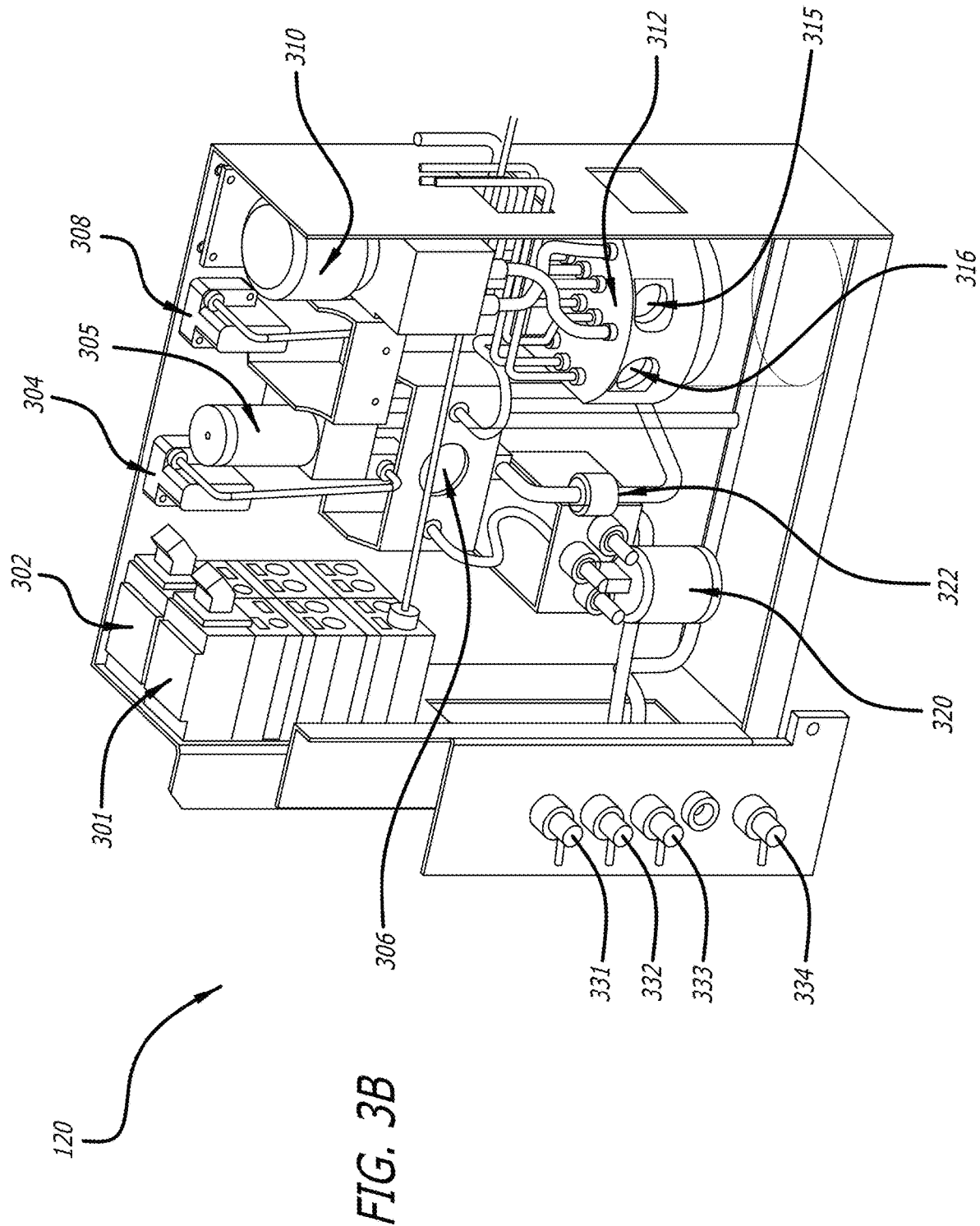

FIGS. 3A-3B illustrate various views of the fluidics bucket 120 which is a part of the fluidics system of the cell sorter system 100. FIG. 18 illustrates a schematic diagram of elements in the fluids bucket 120.

In FIG. 3B, the fluidic bucket 120 includes a sample regulator 301 and a sheath regulator 302 that control the fluidic pressure of the sample fluid and the sheath fluid, respectively. The fluidics bucket 120 further includes a degasser switch 304 and a degasser pump 305 to provide air pressure so that the degasser 306 can remove bubbles from the sheath fluid. The fluidics bucket further includes an aspirator pump 310 to externally aspirate waste out of the cell sorter system through the waste output port 334. The valve manifold 312 includes a plurality of valves to control the fluid system and a sample transducer 315 and a sheath transducer 316. The fluidics input output panel 104 includes a supply air input 331, a sheath air output 332, a sheath fluid input 333, and a waste output 334. The sheath fluid 333 flows through a sheath filter 320 before entering the fluidics bucket 120 of the flow cytometer system. The fluidics bucket 120 includes a pressure switch that controls the opening pressure of the sample pressure chamber. The aspirator pump 310 maintains the vacuum in the tank below the valve manifold 312.

Flow Cell Assembly

Figure 4A:
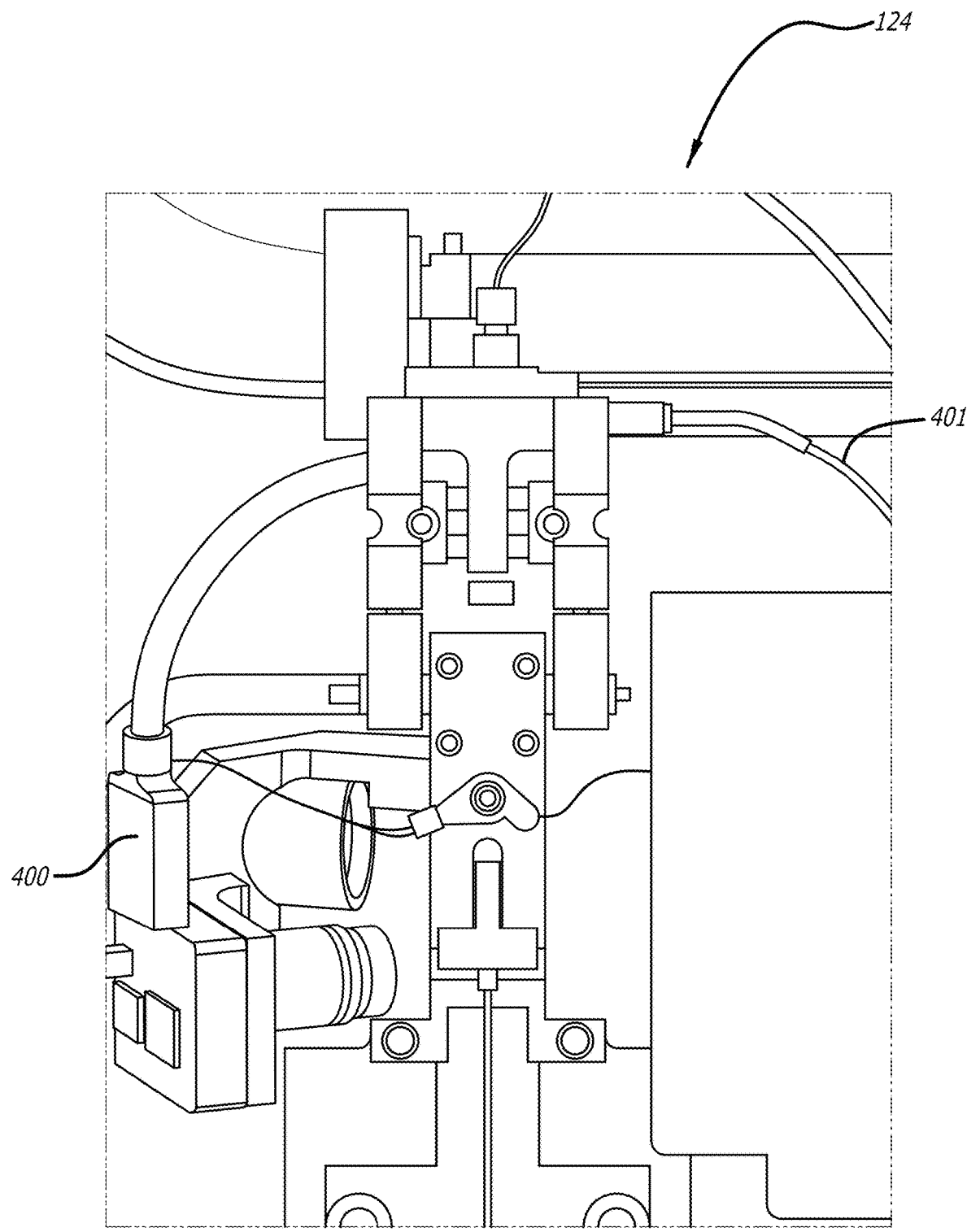
FIGS. 4A-4B are views of the flow cell in the fluidics system of the compact cell sorter system.
Figure 4B:
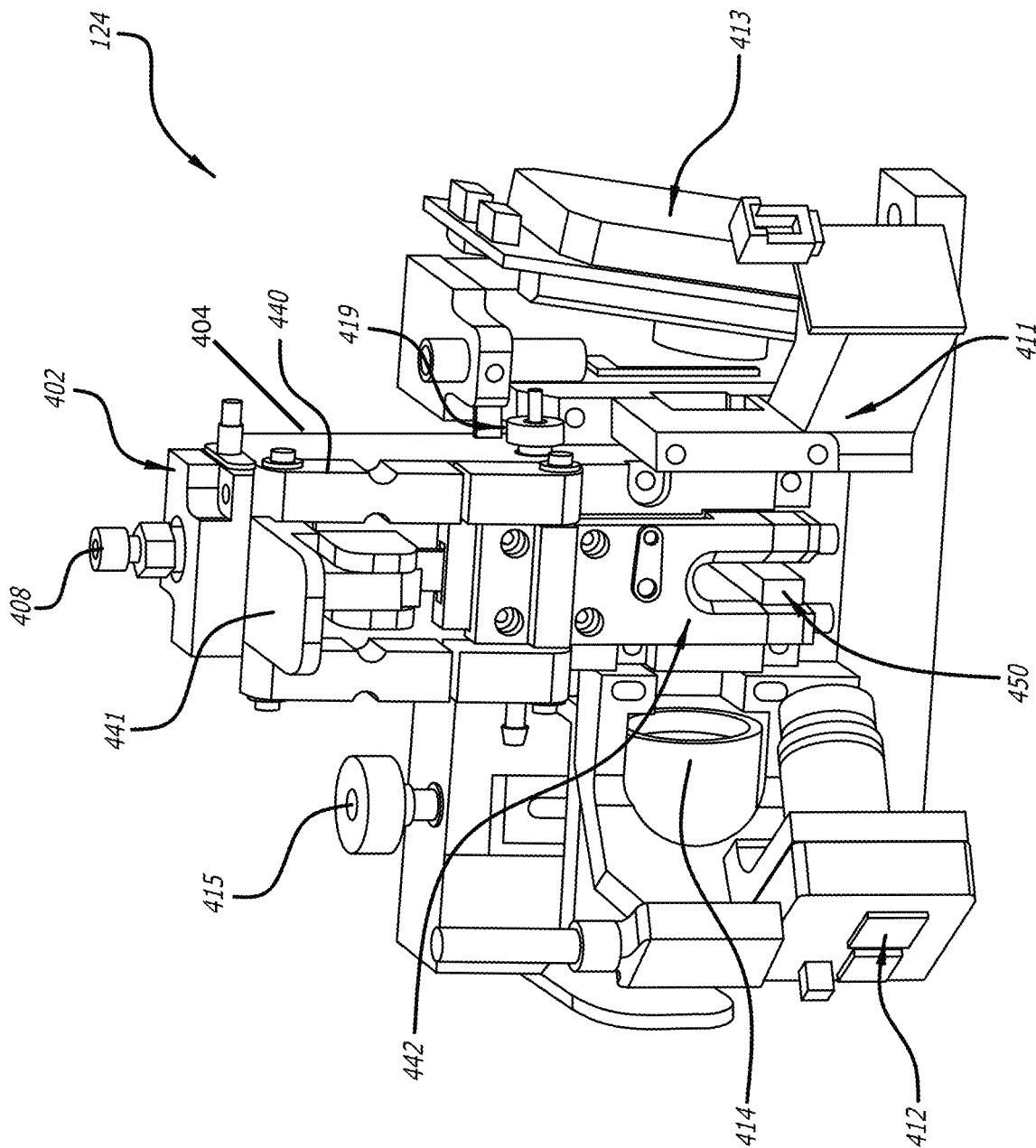

FIGS. 4A-4B illustrate views and components of the flow cell assembly 124. In FIG. 4A, the flow cell 124 has a ground connection 400 to a metal surface. This is to shield the sample fluid from charges being generated by the deflection unit and to remove charges that may have been already present.

Referring now to FIG. 4B, the flow cell 124 includes a drop drive assembly 402, the nozzle assembly 450 and nozzle carriage assembly 442 a carriage release lever 441 of a flow cell linkage 440. The flow cell 124 has a number of optical components including a drop camera 412, drop strobe assembly 411, forward scatter assembly 413, and a final focus lens 414. The final focus lens 414 can be focused by a final focus adjustment 415. The drop drive assembly 402 has a sample input port 408 to receive a hose or pipe that carries the sample fluid.

The Flow cell 124 receives the sample fluid through the sample inlet port 408. The flow cell 124 receives a sheath fluid through a sheath input port 418. The flow cell 124 surrounds the stream of sample fluid with the sheath fluid. The flow cell 124 includes a conductive drain port fitting 419 threaded into the drain port of the flow cell body 404 to evacuate fluids from chambers inside the flow cell, and to impart charge onto the drops of sample fluid with a cell/particle. An electrical wire and a hose both couple to the conductive drain port fitting 419. The electrical wire is in communication with the sort controller to receive a signal that is synchronized with the drops. Over time the signal may be ground, one or more levels of positive charge voltages (e.g., +150, +300), or one or more levels of negative charge voltages (e.g., −150, −300) to respectively keep a drop uncharged, to positively charge a drop, or to negatively charge.

The flow cell 124 includes a flow cell body 404, a drop drive assembly 402, a cuvette 406, a linkage assembly 440, a carriage assembly 442, and a nozzle assembly 450 with a nozzle 704. The linkage assembly 440 includes a carriage release lever 441 that is pivotal to move the nozzle assembly up and down with respect to the cuvette 406. The drop drive assembly 402 includes a sample injection tube 422. The flow cell 124 further includes one or more objective lenses 460A-460B space in order to capture light in injected into a fiber optic cable.

Laser light from one or more lasers is sent into one or more interrogation regions in the flow channel of a cuvette to excite flowing cells/particles and/or one or more fluorescent dye markers attached thereto that pass by. The flow cell 124 further includes one or more objective lenses 460A-460B in order to capture light (e.g., reflected light, scattered light, fluorescent light) from the cells/particles and/or the one or more fluorescent dyes attached to the cells/particles on one side. On an opposite side, the one or more objective lenses 460A-460B can launch the captured light into a fiber optic cable.

The flow cell 124 includes a flow cell body 404 to receive the drop drive assembly 402. The flow cell body 404 receives the drop drive assembly 402 into its chambers. The nozzle assembly 450 is slid into a mount 452 that is coupled to the carriage assembly. The sample injection tube 422 is preferably formed of glass to avoid surface etching in the presence of drop charging and drop-drive vibration that can cause leakage. The drop drive assembly 402 includes the sample input port 408 to receive the sample fluid.

The sample injection tube 422 is preferably formed of glass to avoid surface etching in the presence of electrical currents in the sheath fluid for drop charging and vibration of the drop-drive for drop separation that can cause leakage. The drop drive assembly 402 includes a sample inlet 408 to receive the sample fluid.

The flow cell 124 includes the drain port/charging port with the conductive hose fitting 419 and the sheath inlet port with its hose fitting 418. The sample injection tube 422 is centered in a chamber within the flow cell body 404. The flow cell 124 includes a rear focus adjustment 463 for the one or more objective lenses. The center optical axes of the objective lenses 460A-460B are shown lined up to receive light only from the cuvette. The objective lens mount 461 assures that the objective lenses 460A-460B remain in alignment. The flow cell body 404 is opaque so that light from other sources, such as ambient, is not captured by the objective lenses for 460A-460B.

The nozzle assembly 450 slides in and out of the mount 452 in order to service or repair components of the nozzle assembly or swap for a different diameter of opening in the nozzle. The nozzle of the nozzle assembly receives a sample flow of fluid from a cuvette and forms drops with preferably a single cell/particle each for sorting out.

Deflecting Chamber

The nozzle, in the nozzle assembly 450 of the flow cell, breaks up the sample fluid into droplets. The drops with cells of interest in a center stream 1699C are sorted out by deflecting drops away from the center stream. The drops are charged so they can be deflected away from the center stream 1699C by charged deflecting plates in the deflection chamber (unit) 122. The drops with cells of interest can be collected into separate vessels (test tubes, wells) by the DDU for further testing in a lab.

Figure 5A:
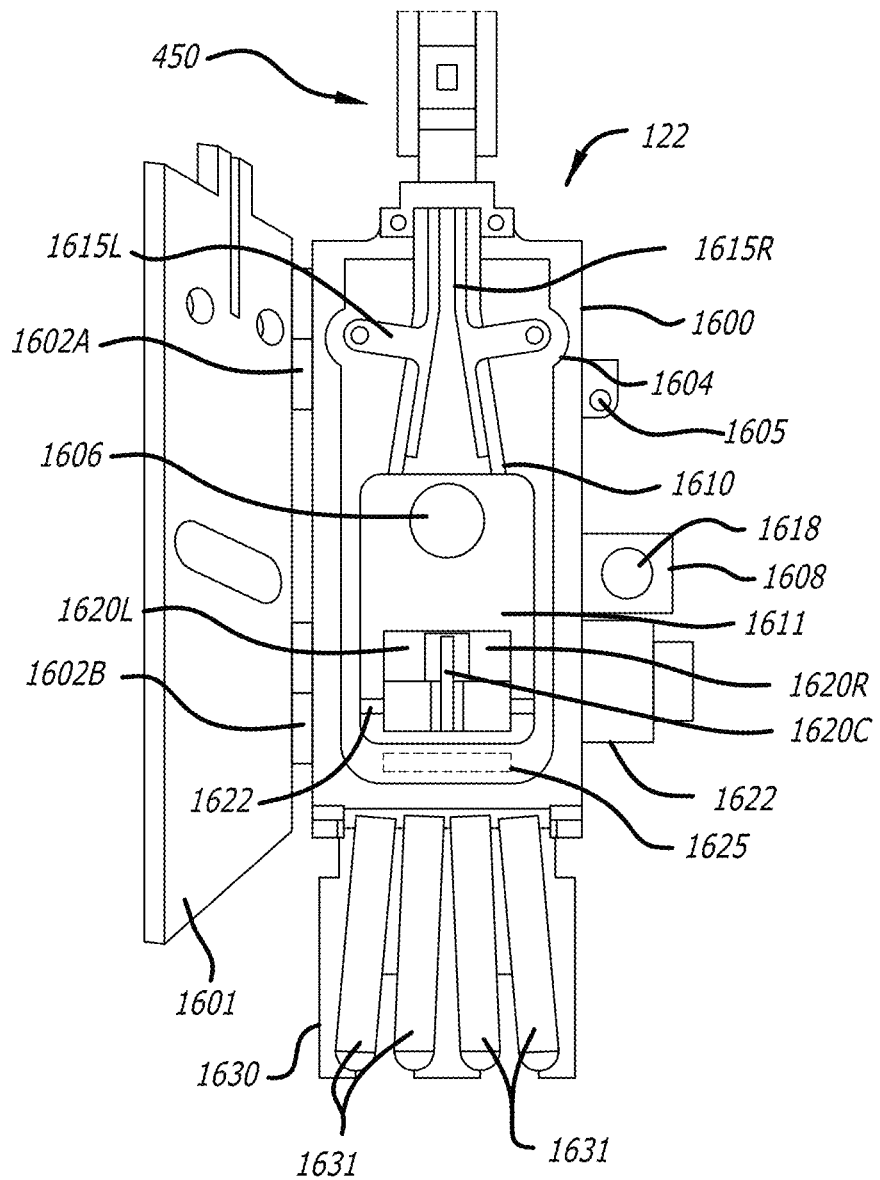
FIG. 5A is a front view of the deflection chamber, with covered removed, of the sorting system of the compact cell sorter system.
Figure 5B:
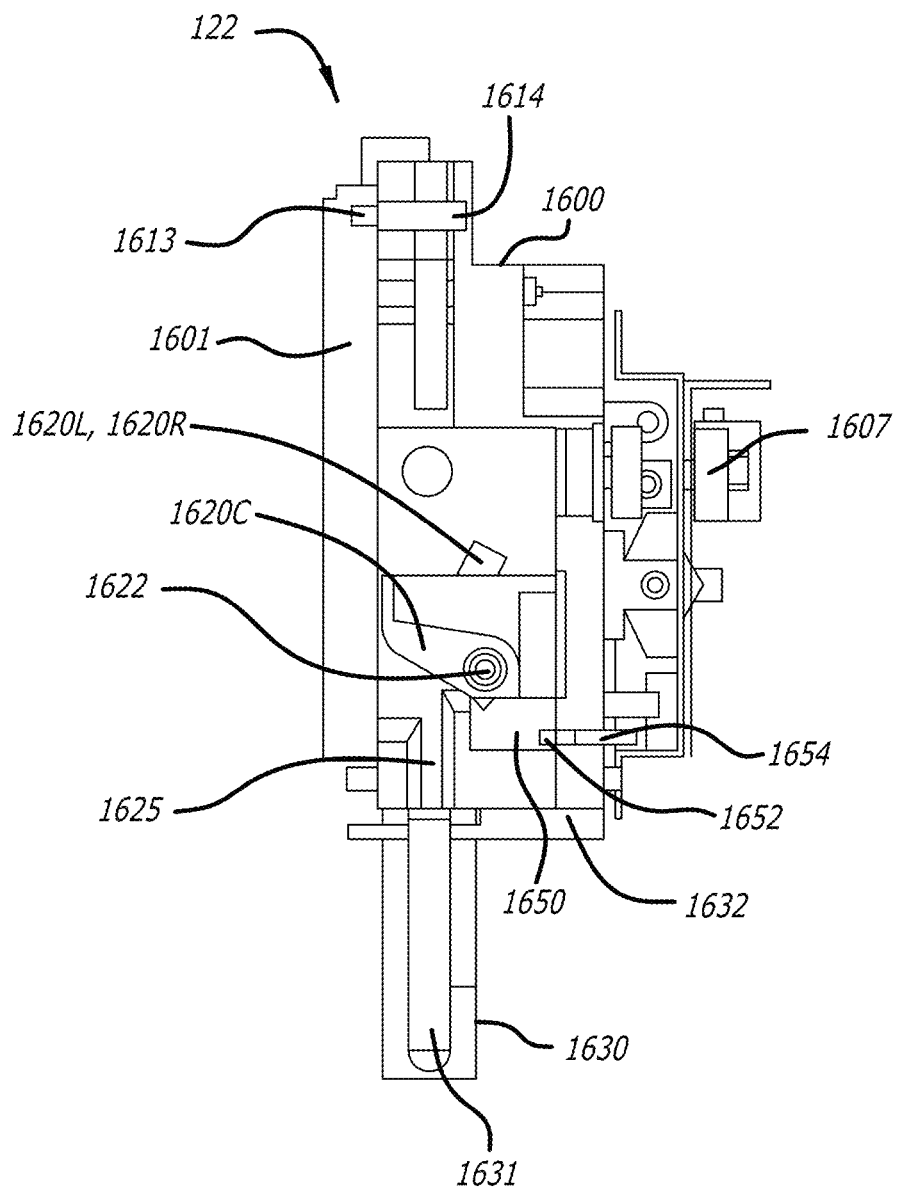
FIG. 5B is a side view of the deflection chamber of the sorting system of the compact cell sorter system.

FIGS. 5A-5B illustrate a deflection (deflecting) unit 122 under the nozzle assembly 450 of the flow cell 124. Accordingly, the deflection unit is in communication with the flow cell 124 to receive a plurality of drops of the sample biological fluid that are in a center stream 1699C. The back of the deflection unit 122 is mounted to a rail so that it can be horizontally adjusted over a range to properly receive the center stream 1699C of drops through an input opening.

The deflection unit 122 includes a case 1600 with a door 1601 pivotally coupled to the case by a plurality of hinges 1602A-1602B on one side (e.g., left side). The door 1601 includes a fastener (catch) 1613 on an opposite side (e.g., right side) of the hinges that can engage a toggle latch 1614 mounted to the case to keep the door securely closed. The case 1600 has a deflection cone cutout 1610 that opens up into a deflection chamber 1611. A seal 1604 is in a channel around the deflection cone cutout 1610 and the deflection chamber 1611 to which the door 1610 presses against. This seals the sample drops within the cutout and chamber so they are not released into ambient air.

A left electrostatic charge (deflection) plate 1615L and a right electrostatic charge (deflection) plate 1615R are mounted in the deflection cone cutout 1610 and are progressively separated further from each other from top to bottom in the cone. A left high voltage charge is applied to the left electrostatic charge plate 1615L and a right high voltage charge of opposite polarity is applied the right electrostatic charge plate 1615R to impose an electrostatic charge field through which droplets pass. If a drop is to be sorted by moving it away from a center stream of drops, a positive charge or a negative charge is synchronously applied to a drop by the conductive hose fitting in the drain/charge port and a charge signal from the sort controller. If the droplets are uncharged (grounded), they remain in the center stream. Only if a droplet is charged, by applying a charge signal (positive or negative) to the charge port on the flow cell, will it be deflected as it passes through the electro static charge field formed by the electrostatic charge plates. The degree of deflection depends on both the magnitude of the electrostatic charge field imparted by the left and right electrostatic charge plates and the polarity and magnitude of the charge imparted to the droplet by the charge port.

For example, the left electrostatic charge plate may be charged at negative 2000 Volts and the right electrostatic charge plate may be charged at positive 2000 volts to provide a 4000 volt electrostatic field between them. The voltages on the electrostatic charge plates are held constant during a sort of droplets in a sample. Droplets then may be selectively charged instantaneously (by applying charge to the conductive hose fitting in the charge/drain port of the flow cell) to achieve a desired deflection away from center. Accordingly, the precise magnitude and polarity of voltage applied to cells associated with each stream path will depend on the desired direction and magnitude of deflection needed to get the droplet into a receiving receptacle. Accordingly, multiple (e.g., 2, 3, 4, 5, 6) left deflected stream paths and multiple (e.g., 2, 3, 4, 5, 6) right deflected stream paths of drops of sample biological fluid can be formed about the center stream path 1699C. For simplicity of the explanation herein, we will collectively refer to them herein as a left stream path (left stream) 1699L and a right stream path (right stream) 1699R.

A backside of the case 1600 has a side laser window and a stream camera window 1606. A side laser light generated by a laser 1608 is directed into the deflection chamber 1611 through the side laser window. The position of the laser 1608 behind the side laser window can be adjusted by the laser position adjuster 1618. The side laser light is adjusted front to back to strike the drops of biological fluid to sense the path position of the drops. A stream camera 1607 is mounted outside the case in line with and behind the stream camera window 1606 to view the drops and determine whether or not they are in a center stream path 1699C, a left deflected stream path 1699L, or a right deflected stream path 1699R.

The stream camera 1607 provides a feedback mechanism to the sort controller to be sure the charges on the charge plates are appropriate for deflection of drops into the left deflected stream path 1699L and the right deflected stream path 1699R, as well as equally charged (or no charge) for dropping in the center stream path 1699C inside the deflection unit 122.

At the base of the deflection chamber 1611 is an aspirator well (tub) 1650 with a drain to aspirate drops into the waste line out of the cell sorter. In front and below the tub in the base of the deflection chamber is a horizontal drop slot 1625. Inside the chamber 1611, a left pivotal sidestream scupper 1620L, a non-pivotal center collector 1620C, and a right pivotal sidestream scupper 1620R are mounted along a drive shaft 1622 in the tub of the deflection chamber. The non-pivotal center collector 1620C is around the drive shaft between the left and right pivotal sidestream scuppers but is undriven by the drive shaft. The left pivotal sidestream scupper and the right pivotal sidestream scupper pivot with the drive shaft between a raised position and a lowered position. The non-pivotal center collector 1620C is non-pivotal and remains in a fixed rotational position regardless, but is free to move left and right with the scuppers. Drops that are deflected and not captured by the sidestream scuppers 1620L-1620R or the center collector 1620C can fall out of the deflection unit 122 through the drop slot 1625.

With no deflection by the electrostatic charge (deflection) plates, the center stream of drops from the nozzle assembly drop through the deflection cone 1610 into the deflection chamber 1611 and are caught by the center collector 1620C. The center collector 1620C and the sidestream scuppers 1620L-1620R, when in the lowered position, act somewhat like rain gutters directing the flow of drops of sample fluid. The center collector 1620C directs the drops it catches into the tub 1650 for aspiration down the drain 1652 as waste. In a lowered position, the left and right pivotal sidestream scuppers 1620L-1620R catch drops that are deflected away from the center stream 1699C and direct the drops they catch by means of a tunnel into the tub 1650 for aspiration down a drain 1652 as waste. As can be seen in FIG. 5B, the drops in the tub 1650 can be aspirated down the drain 1652 and out through the waste port (waste outlet) 1654 by a vacuum.

In a raised position, the left and right pivotal sidestream scuppers 1620L-1620R do not catch any drops. When left and right pivotal sidestream scuppers are in the raised position and selected drops are deflected away from the center stream as deflected drops, those deflected drops of sample fluid drop past the sidestream scuppers and through the drop slot 1625 in the base of the case 1600. The deflected drops pass through the drop slot 1625 for collection in the DDU chamber 128 below the deflection unit 122.

In the case of an urgent sorter shutdown, the sorter 100 pivots the shaft and the sidestream scuppers into the lowered position such that they and the center non-pivotal collector 1620C catch all drops of sample fluid formed by the nozzle assembly 450, whether deflected or not, and direct the drops into the tub 1652 for aspiration down the drain and out the waste port (waste outlet) 1654.

Figure 5D:
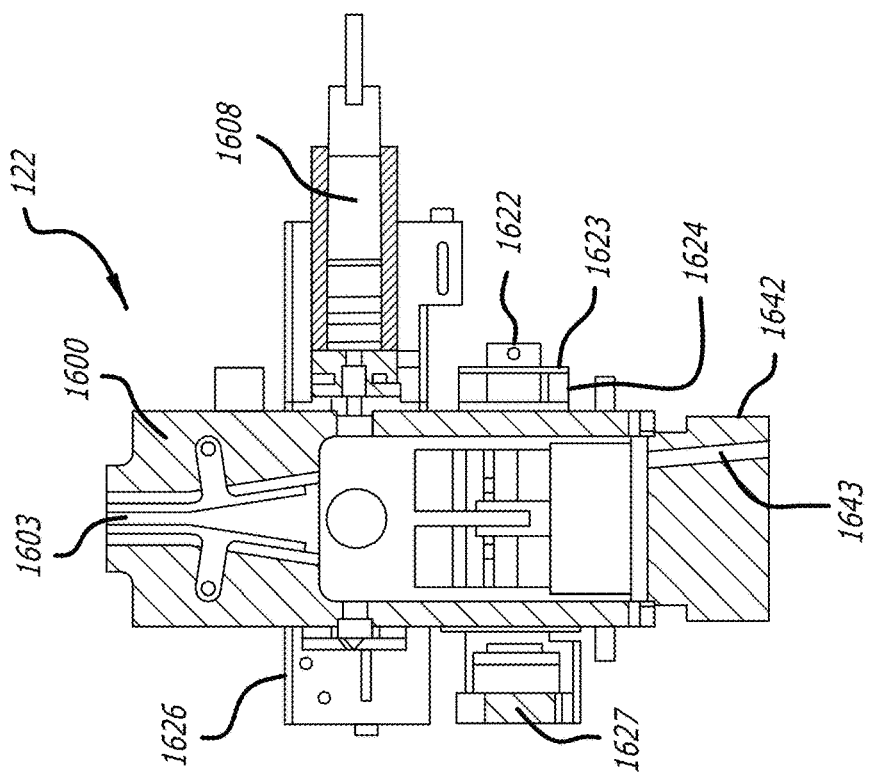
FIG. 5D is a cross sectional view of the deflection chamber of the sorting system of the compact cell sorter system with a plate guide to guide droplets into one of the plurality of wells of a well plate.
Figure 5C:
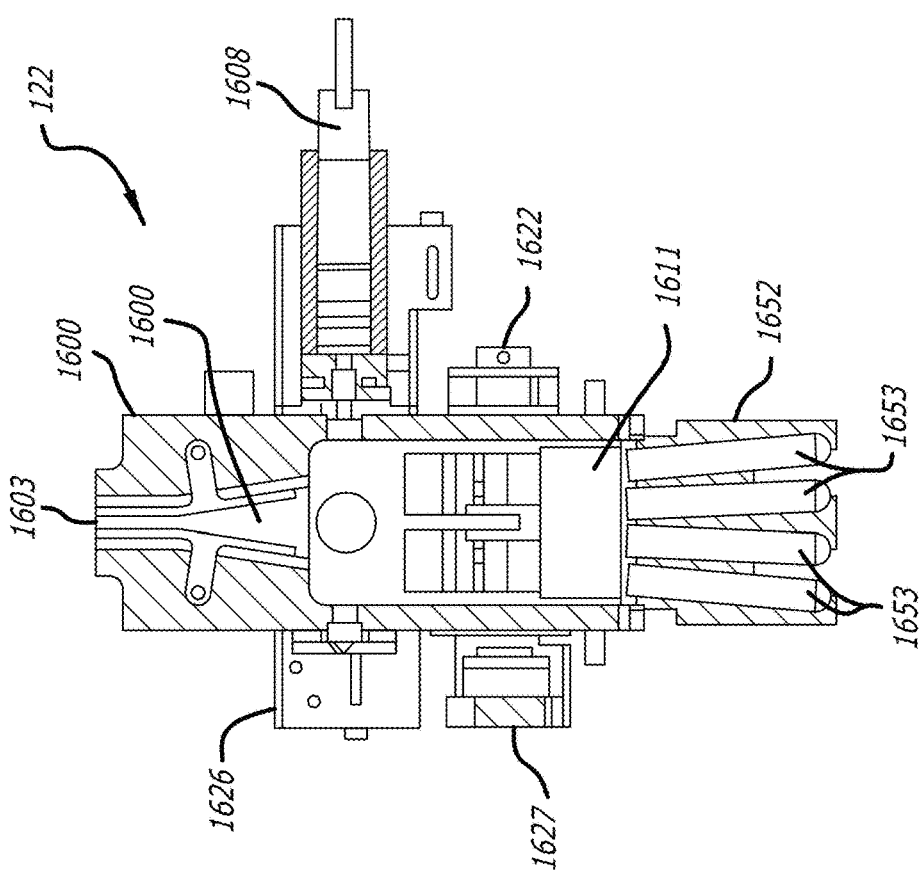
FIG. 5C is a cross sectional view of the deflection chamber of the sorting system of the compact cell sorter system with a four tube collection holder.
Figure 5G:
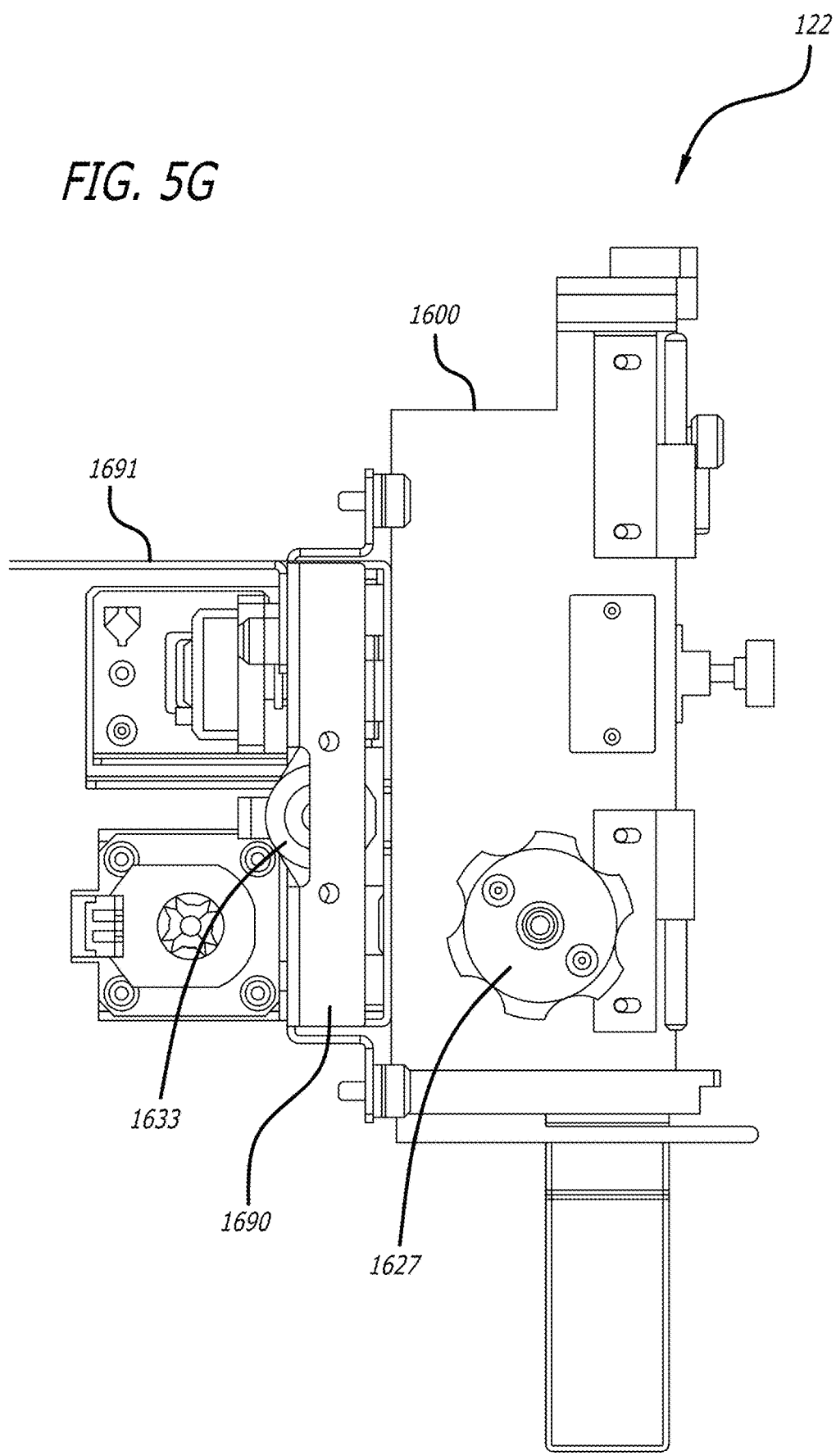
FIG. 5G is a left side view of the deflection unit, with cover removed, of the sorting system of the compact cell sorter system.

As shown in FIGS. 5C-5D, ends of the drive shaft 1622 extend outside the chamber 1611. A scupper pulley 1623 is mounted to the shaft 1622 near one end (e.g., right end). A reversable electric motor has a shaft with appropriately sized drive pulley. As shown in FIG. 5E, a continuous (circular) belt 1624 is mounted between the drive pulley 1683 and the scupper pulley 1623 to pivot the shaft 1622 in response to the rotation by the reversable electric motor and raise or lower the sidestream scuppers.

The deflection unit (chamber) 122 is horizontally adjustable. The deflection unit 122 can be slidingly mounted to a rail 1626 as shown in FIGS. 5C-5D and horizontally adjustable from side to side, in order to adjust its position to the center stream path 1699C of drops that enter at a top opening 1603. The deflection unit 122 can be horizontally adjusted so that the center stream 1699C of drops is selectively positioned (equidistant or as otherwise desired) between the left charge plate 1615L and the right charge 1615R plate as the drops enter the deflection cone cutout 1610.

Figure 5H:
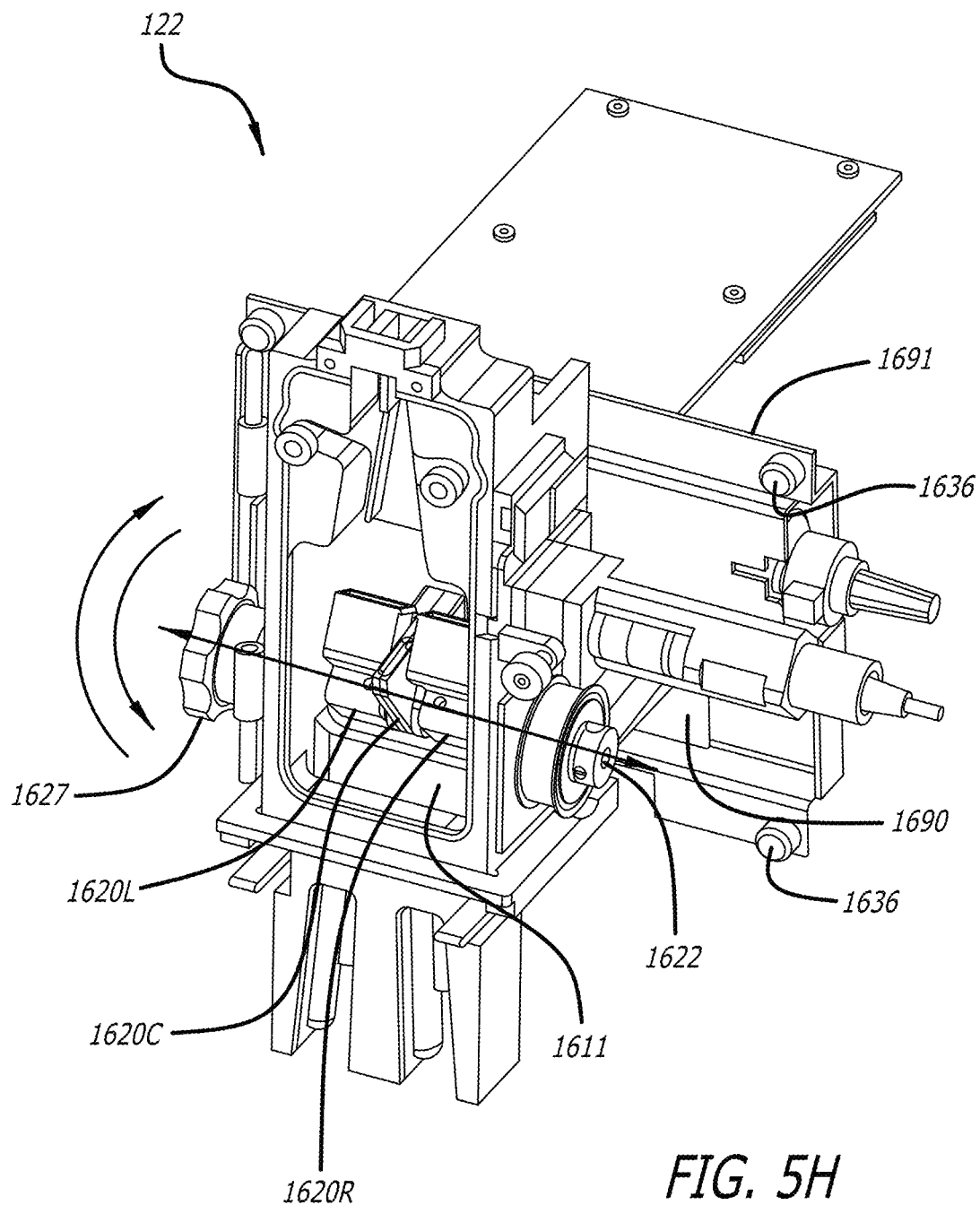
FIG. 5H is a perspective view of the deflection unit, with cover removed, to show the side to side movement of scuppers in the deflection chamber to align the center aspirator with the center stream of drops.

Because the drops can be initially charged and the charge plates may unequally influence entering drops, the left pivotal sidestream scupper 1620L, the center non-pivotal collector 1620C, and the right pivotal sidestream scupper 1620R are horizontally adjustable together from side to side along the drive shaft 1622, such as shown in FIG. 5H. An adjustment knob 1627 shown in FIGS. 5C-5D,5G-5H is provided to horizontally adjust the position of the scuppers 1620L-1620R and the center collector 1620C together along the shaft 1622. Accordingly, without charges deflecting the stream of drops, the center non-pivotal collector 1620C can be centered under the center stream 1699C of drops of sample fluid with an adjustment to direct the drops into the tub and down the drain to aspirate them out from the cell sorter through the waste outlet.

Figure 5I:
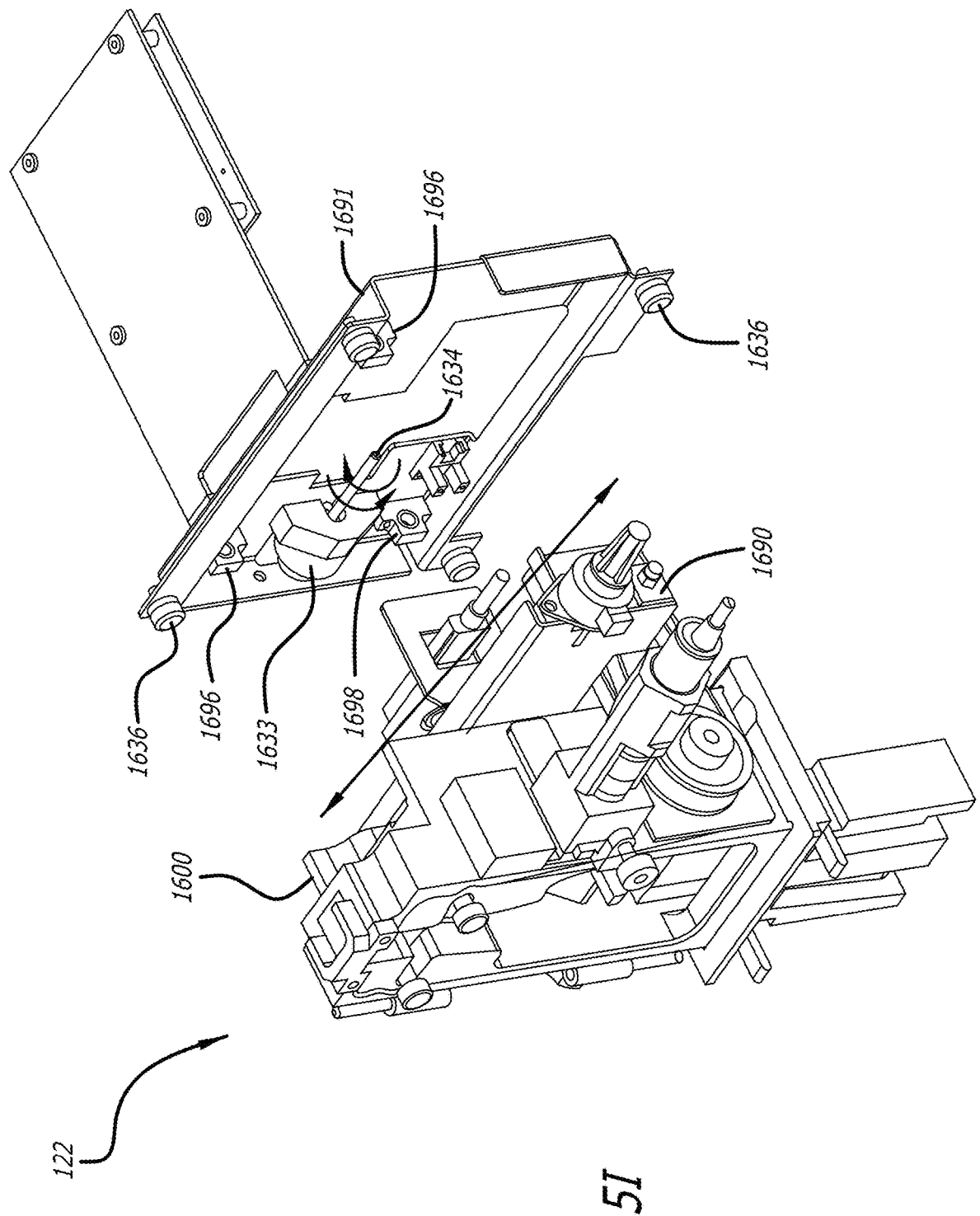
FIG. 5I is a frontal perspective view from the right side of the deflection unit, with covered removed, separated from the rail system to show movement of the deflection chamber sideways (side-to-side) to align with the center stream of drops into the deflection unit.
Figure 5J:
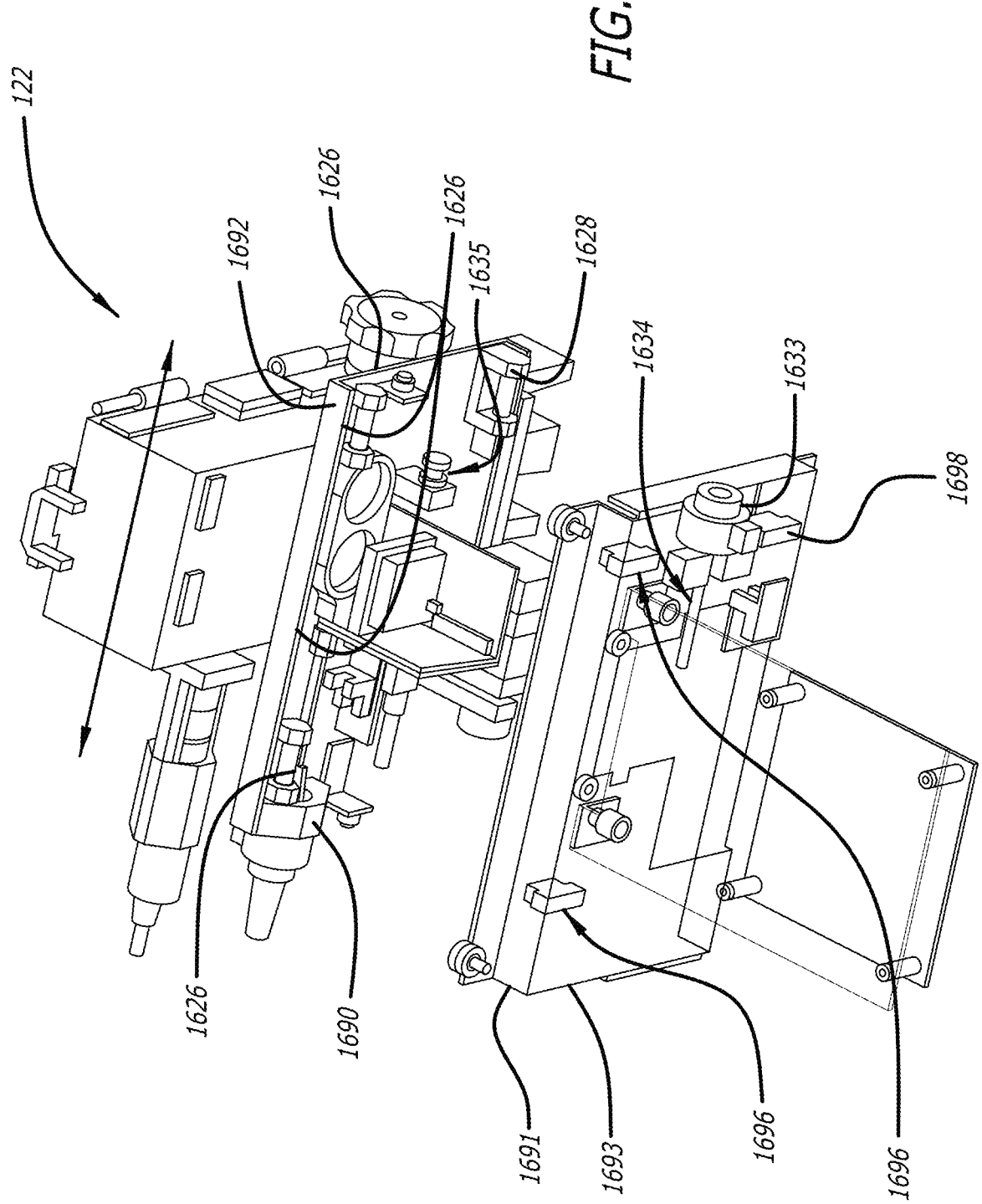
FIG. 5J is a back perspective view of the deflection unit separated from the rail system to show movement of the deflection chamber sideways (side-to-side) to align with the center stream of drops into the deflection chamber.
Figure 5K:
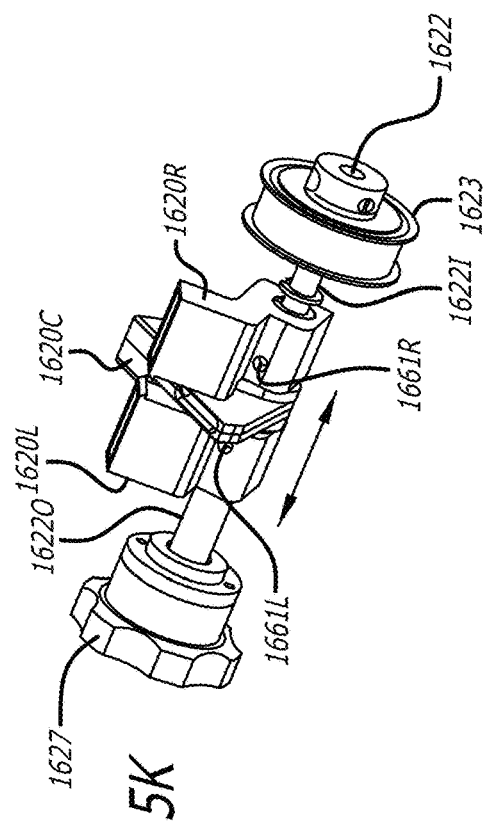
FIG. 5K is a perspective view of the scuppers, aspirator, and transmission shaft removed from the deflection unit.
Figure 5L:
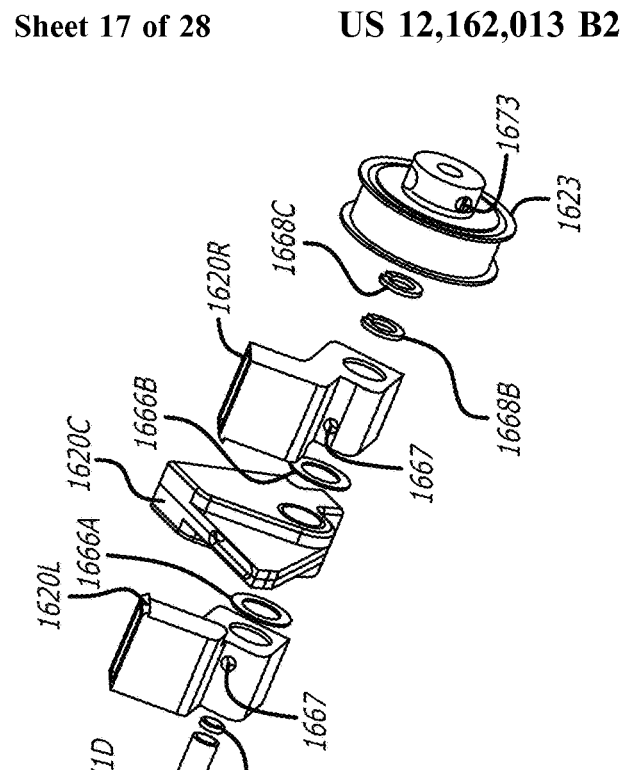
FIG. 5L is an exploded view of the scuppers, aspirator, and transmission shaft removed from the deflection unit.
Figure 5L:
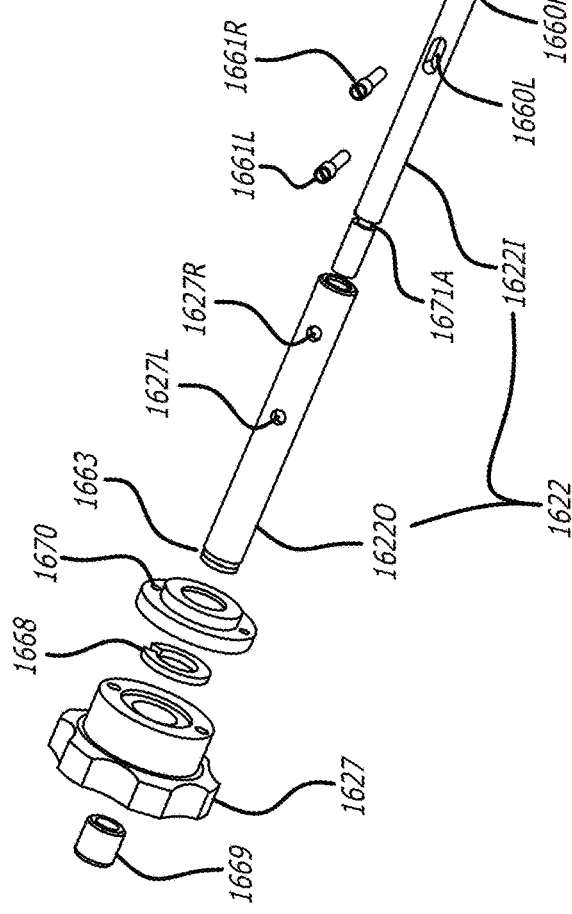
Figure 5M:
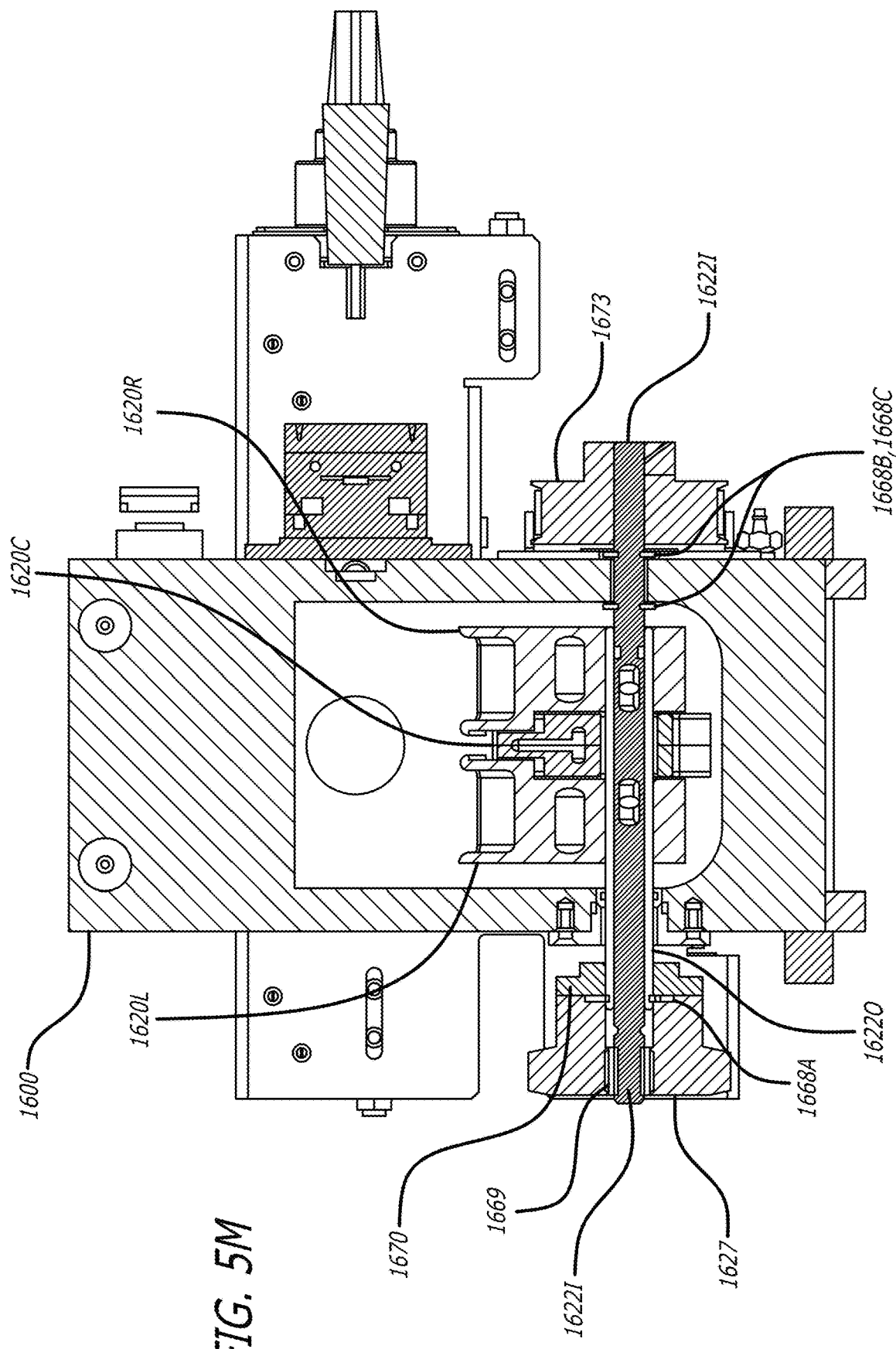
FIG. 5M is a cross sectional view of the deflection unit to better show the assembly of the scuppers, aspirator, and transmission shaft.

FIG. 5K shows an isolated view of the sidestream scuppers, center collector, shaft, pully and knob assembled together out of the deflection subsystem 122. FIG. 5L shows an exploded view of the left and right sidestream scuppers 1620L-1620R, center collector 1620C, shaft 1622, pully 1623, and the adjustment knob 1627. With the center collector 1620C sandwiched between the left and right sidestream scuppers 1620L-1620R, the adjustment knob 1627 can be used to horizontally move then along the shaft 1622.

As best seen in FIG. 5L, an exploded view, the shaft 1622 includes an inner shaft 1622I over which an outer shaft 1622O can slide. However, the inner shaft 1622I and the outer shaft 1622O can rotate together. The pulley 1623 is mounted near an end of the inner shaft 1622I and driven by a belt. The left and right sidestream scuppers 1620L-1620R are mounted to the outer shaft 1622O by left and right screws 1661L-1661R inserted through openings 1667 in each of the sidestream scuppers 1620L-1620R and threaded into threaded openings 1672L-1672R, respectively. The ends of the screws 1661L-1661R are input into left and right oval slots 1660L-1660R respectively to allow horizontal movement of the scuppers and the outer shaft 1622O along the inner shaft. However, the rotational torque on the inner shaft 1622I is transferred by the screws 1661L-1661R to the outer shaft 1622O and the scuppers. The center collector 1620C is slidingly mounted around the outer shaft 1622O so that it can turn freely without interference. That is, when the inner and outer shafts are rotated by the pulley 1623, the center collector 1620C does not rotate.

A threaded metal sleeve 1669 is pressed into the adjustment knob 1627 to form a unitary piece. The threaded metal sleeve 1669 engages threads on the end of the inner shaft 1622I to horizontally adjust the outer shaft (along with the sidestream scuppers and the center aspirator) with respect to the case 1600 of the deflection unit 122. Circlip 1668A transfers the horizontal motion of the threaded knob 1627 (along the threaded part of inner shaft 1622I) to outer shaft 1622O. The outer shaft 1622O passes through the collar 1670. Circlip 1668A is installed over the ring grooved end of the outer shaft 1622O. The adjustment knob 1727 is screwed to the collar 1670, thereby confining the circlip 1668 between the adjustment knob and collar.

A plurality of washers (e.g., washers 1666A-1666B) can be used along the outer shaft 1622O to reduce friction with the non-rotating center aspirator and the inner sides of the case. An O-ring 1619 is mounted in the ring slot 1671B to minimize liquid intrusion between the inner and outer shafts. To keep the inner shaft horizontally fixed with respect to the case 1600, a plurality of circlips (e.g., circlips 1668B-1668C) are coupled into a plurality of ring slots (e.g., ring slots 1671C-1671D) of the inner shaft 1622I thereby locating the right side of the inner shaft end with respect to the right side opening in the case. The ends of inner shaft extend through the tub and outside through left and right side openings in the case. One end of the outer shaft extends through the tub and outside the case through the left side opening. The adjustment knob 1727, the threaded sleeve 1669, and collar 1670 mount outside the case 1600 over left ends of the inner shaft and outer shaft. The pulley 1623 mounts over the right end of the inner shaft. The pulley includes a set screw 1673 to couple the pulley and the inner shaft rotationally together.

FIG. 5H illustrates rotation of the adjustment knob 1627 and the horizontal adjustment in the outer shaft 1622O along the inner shaft 1622I. Within the tub, the sidestream scuppers 1620L-1620R, and the center collector 1620C are adjusted horizontally together with the outer shaft. Rotating the adjustment knob 1727 against the case 1600 in one direction (e.g., counter clockwise) pulls the outer shaft 1622O horizontally in one direction (e.g., to the left) along the inner shaft 1622I. Rotating the adjustment knob 1727 against the case 1600 in the opposite direction (e.g., clockwise) pushes the outer shaft 1622O horizontally in the opposite (e.g., to the right) direction along the inner shaft 1622I. Obviously, the threads can be changed so that the rotations in the knob can be opposite with the same horizontal directions.

As shown in FIG. 5E, the pulley 1623 coupled to the shaft 1622I is rotationally driven by a belt 1624 that is mounted to the pulley 1683. The pulley 1683 is coupled to a shaft 1681 that is driven by a reversable electric motor 1680. A portion of the door hinges 1620A, 1620B mounted to the case 1600 can be seen with the door removed. The toggle latch 1614 mounted to the case/housing 1600 is shown ready to engage the catch of the door. The position of the laser light can be adjusted by turning a threaded knob 1609 to move the laser 1608 forward or backward with respect to the case 1600.

As mentioned herein, the entire deflection unit 122 is horizontally adjustable in order to position how the center stream path 1699C of drops from the flow cell 124 enter into the deflection unit 122 through a top opening 1603. FIGS. 5I-5J illustrate how the deflection unit 122 can be horizontally adjusted left or right by an electric motor 1633. As better seen in the partial exploded views of FIGS. 5I-5J, the deflection unit 122 further includes a back plane 1690 and a back mount 1691 slidingly engages the back plane 1690. The front side of the back plane 1690 is coupled to the back side of the case 1600. The back side of the back mount 1691 can couple to the chassis or frame of the cell sorter system 100 by a plurality of fasteners (e.g., bolts or screws).

The back plane 1690 can slidingly engage the back mount 1691 and be horizontally adjusted by a reversable electric motor 1633 with a lead screw 1634 mounted to its shaft. As best seen in FIG. 5J, the back plane 1690 includes a frame 1692 with a back side having a pair of top guide rails 1626 mounted near the top and near the left and right sides. The back plane 1690 further includes at least one lower guide rail 1628 mounted near the bottom of the back side of the frame 1692 on one side (e.g., the left side). A threaded lead screw nut 1635 is also mounted to the back side of the frame 1692 and is configured to engage the threaded lead screw 1634.

The back mount 1691 includes a frame 1693 with a front side to which the reversable electric motor 1633 is mounted. The back mount 1691 further includes a pair of top guides 1696 mounted to the front side near the top and left and right sides of the frame 1693. The back mount 1691 further includes at least one lower guide 1698 mounted to the front side near the bottom of at least one side (e.g., left side) of the frame 1693. The pair of top guides 1696 and the at least one lower guide 1698 of the back mount 1691 of the back mount slidingly engage with the pair of top guide rails 1626 and at least one lower guide rail 1628, respectively, in the back plane.

With the threaded lead screw 1634 engaged with the threaded lead screw nut 1635, the horizontal adjustment of the deflection unit 122 with respect to the back mount is controlled by the reversable motor 1633. The reversable motor 1633 turns its shaft and the lead screw 1634 in one direction to push the backplane 1690 and deflection unit in one direction (e.g., left). The reversable motor 1633 turns its shaft and the lead screw 1634 in the opposite direction to pull the backplane 1690 and deflection unit in the opposite direction (e.g., right). A user may monitor the position of the center stream 1699C of drops with respect to the top opening 1603 and the deflection plates and adjust the horizontal position of the deflection unit 122 under manual software control. A front or backside camera, if available to view the center stream 1699C, can be used to monitor the position of the center stream path 1699C, provide feedback to a control system, and automatically position the deflection unit 122 with the center stream.

As mentioned herein, the deflected drops pass through the drop slot 1625 in the case 1600 for collection in the drop collection (confinement) chamber 128 below the deflection unit 122. The deflection unit 122 includes a collection retainer 1632 in the drop collection (confinement) chamber 128 that is coupled in communication with the case 1600. The collection retainer 1632 includes a pair of rails around an opening in a DDU case 200. A tube or sort collection holder 1630 can be slid into the pair of rails of the collection retainer in the drop collection/loading chamber 128. The sort collection holder 1630 includes a plurality of tube slots 1631 to receive a plurality of test tubes 34, such as show in FIG. 1A. A plurality of test tubes 34 may be inserted into the slots/openings 1631 in the sort collection holder 1630 to receive the drops sorted out by the cell sorter. As shown in FIG. 5B, the openings 1631 are aligned (front to back in depth) with the drop slot 1625 such that test tubes mounted therein can capture drops of sample fluid.

Drops in one or more left deflected stream paths may be received in test tubes to the left of center. Drops in one or more right deflected stream paths may be received in test tubes to the right of center. FIG. 5C illustrates a four tube sort collection holder 1652 coupled to the case 200 with four openings 1653 to hold four test tubes, two test tubes to receive drops in two left deflected stream paths and two test tubes to receive drops in two right deflected stream paths.

FIG. 5D illustrates a plate guide 1642 instead of a tube or sort collection holder. The plate guide 1642 has a stream path opening 1643 in which selected drops fall through and out of the plate guide. A collection plate 35, such as shown in FIG. 1A, with a plurality of wells is moved around underneath the plate guide by the loading system to catch drops in the one or more wells. A collection plate can have a plurality of wells (e.g., 32 or 64) in which to capture drops with different types of cells/particles. The plate coupled to the top of a magnetic puck. The magnetic puck that slides along the separation plate by a magnetically coupled driver. The collection plate is moved to align a selected well underneath the stream path opening 1643 to receive the drops of sample fluid with the desired cells/particles.

Sample Input Station

Figure 6A:
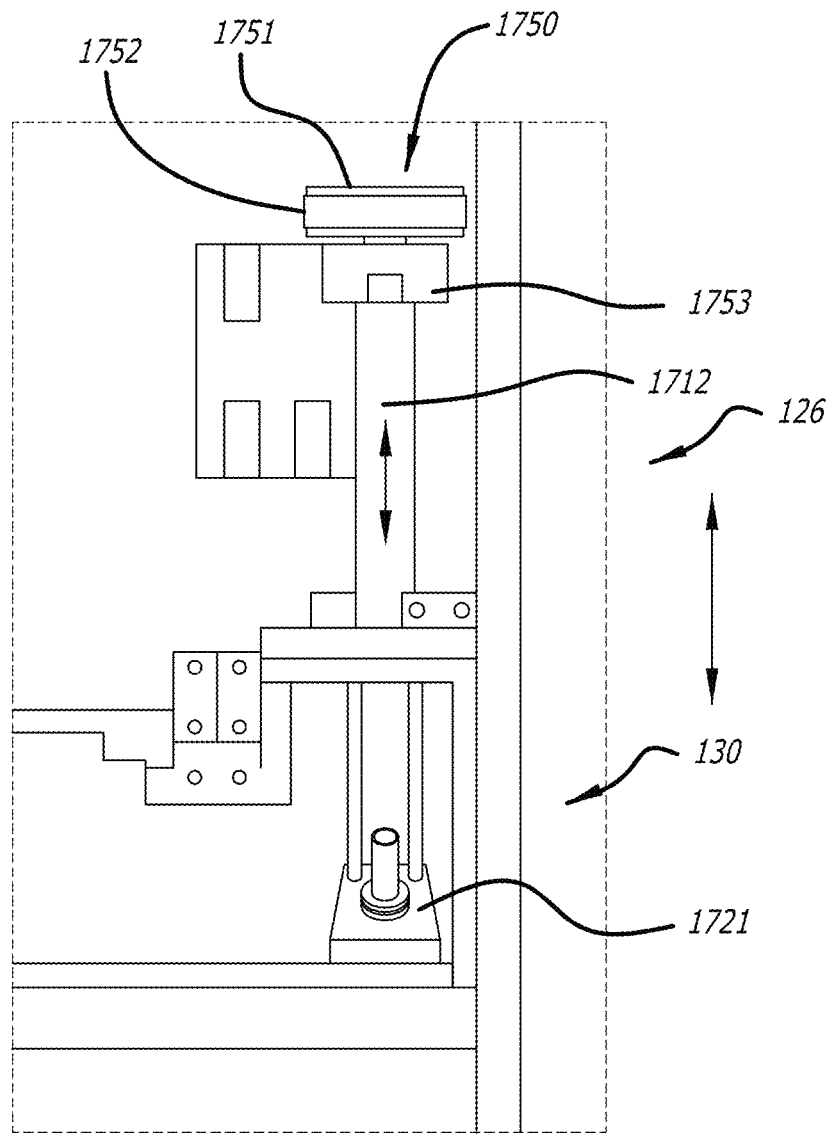
FIGS. 6A-6C are views of the sample input station (SIS) of the compact cell sorter system.
Figure 6B:
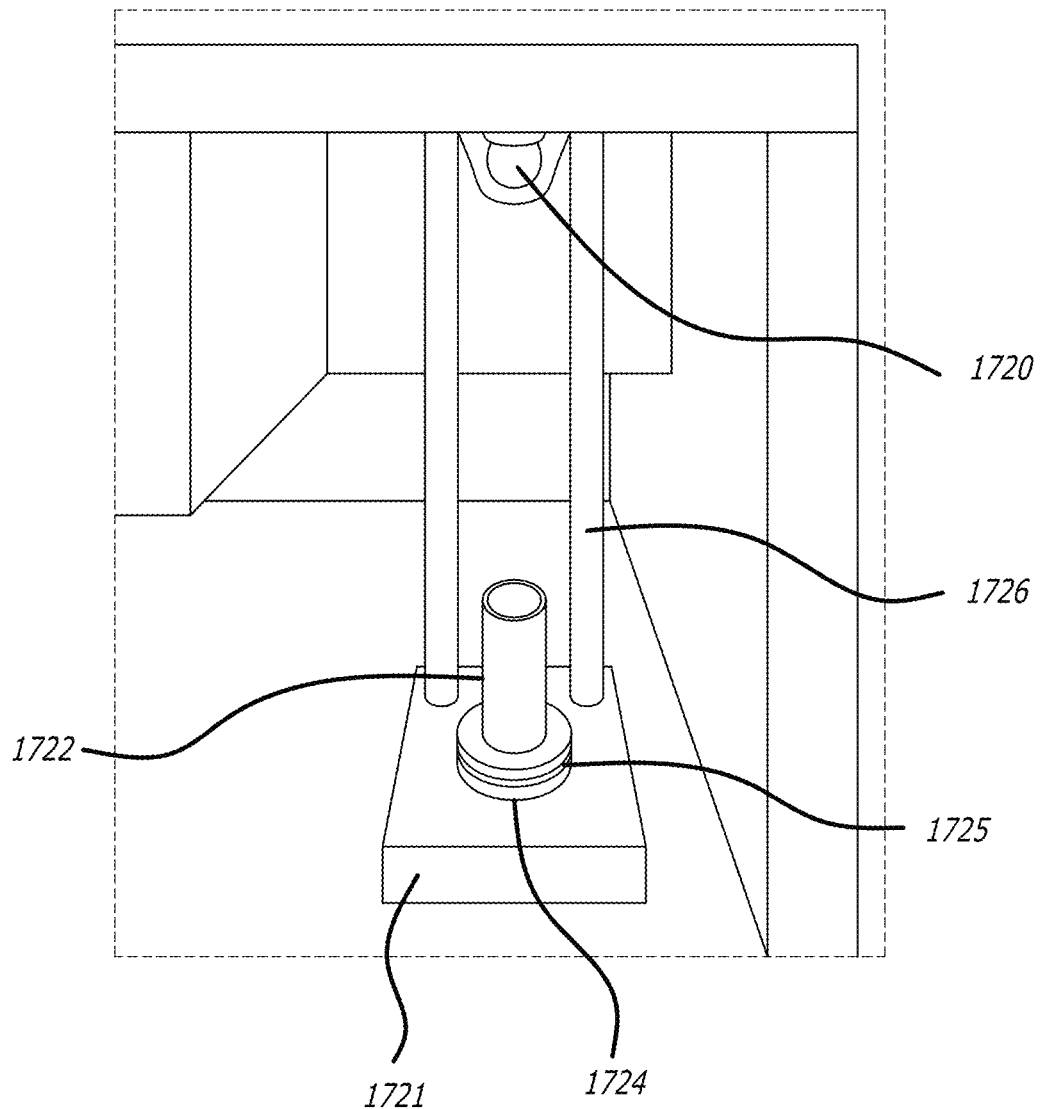
Figure 6C:
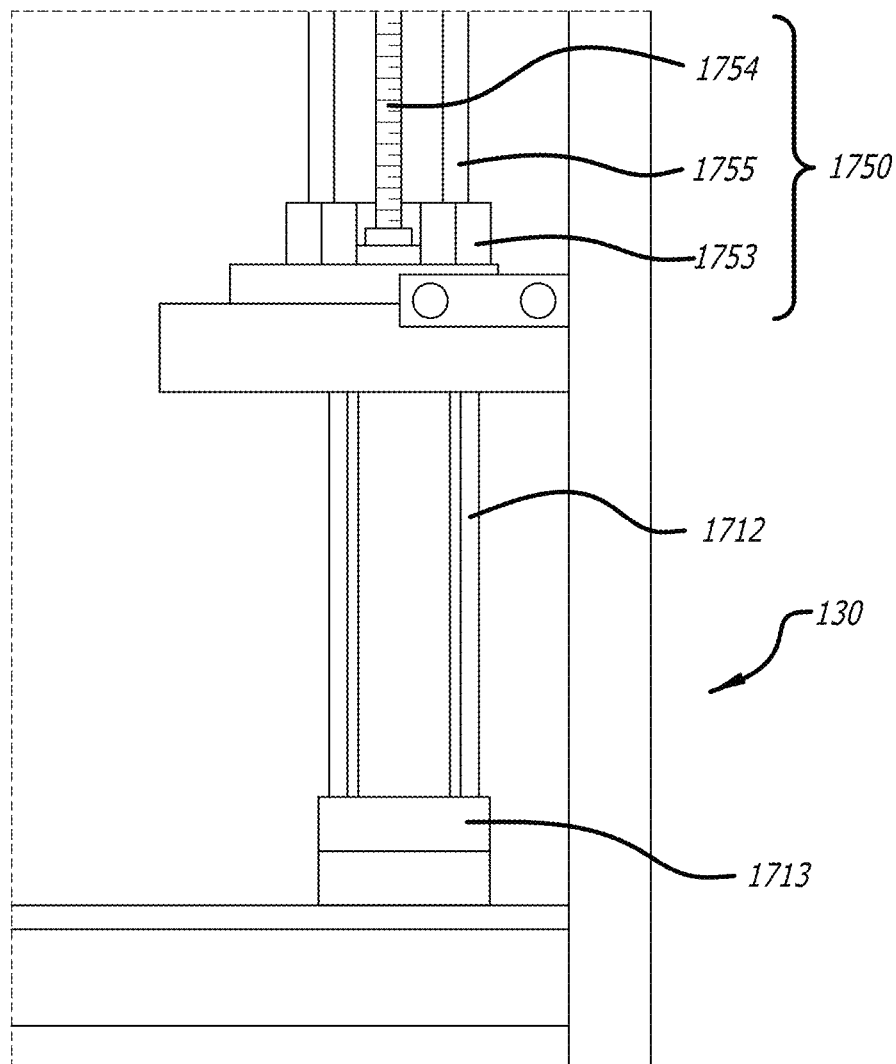

FIGS. 6A-6C illustrate views of the sample input station 130. The sample input station (SIS) 130 includes a moveable pressure chamber (pressure cylinder) 126 with a chamber body 1712 that moves up and down by a threaded drive mechanism 1750 guided by a pair of guide rods 1750. The SIS 130 further includes, without limitation, an aspirator 1720, a tube holder 1722, and an agitation stage 1724.

FIG. 6A-6B illustrate an open position of the pressure chamber (pressure cylinder) 126 of the sample input station (SIS) 130. In contrast, FIG. 17C illustrates the closed position of the pressure chamber (pressure cylinder) 126. The chamber 1712 is driven down into the closed position over the agitation stage 1724 as shown in FIG. 6B. A top switch and a bottom switch are used to sense the two positions (open and closed) of chamber body 1712 over which the threaded drive mechanism 1750 can run and the points at which it should stop.

Sample test tubes (e.g., Fluorescence Activated Cell Sorting (FACS) tubes) can be mounted in the tube holder 1722. A cell strainer may be used to filter out certain types of cells. The moveable pressure chamber (pressure cylinder) 126 includes a sample input tube 1912 that is insertable into the test tubes as it is lowered into closed position. The sample input tube 1912 can be flushed by a fluid, such as water or sheath fluid, before reusing the sample input tube on the next test tube. With the moveable pressure chamber (pressure cylinder) 126 in the down position, the air in the moveable pressure chamber (pressure cylinder) 126 can be pressurized to force sample fluid into the sample input tube 1912.

As shown in FIG. 6C, the drive mechanism 1750 includes a male threaded lead screw 1754 engaged with a female threaded nut in a platform 1753. The platform 1753 is coupled to the chamber body 1712 at the bottom by means of a single guide rod and a base plate to raise and lower the pressure chamber (pressure cylinder) 126 as the drive mechanism is activated. The platform 1753 includes a pair of openings over a pair of upper guide rods 1755 to maintain the orientation of the platform and guide it up and down. As shown in FIG. 6A, a driven pulley 1751 is mounted near an end of a threaded lead screw of the threaded drive mechanism 1750. A continuous (circular) belt 1752 is mounted to the driven pulley 1751. At the opposite end of the belt 1752, in the back of the system 100, a drive pulley is coupled to a shaft of a reversable electric motor to rotate the belt and pulley 1751 to turn the threaded lead screw 1754 until reaching the top and bottom switches. The bottom base of the chamber body 1712 is coupled to the threaded nut platform 1753 with a single guide rod. The threaded lead screw 1754 is coupled to the threaded nut platform. A bottom open end of the chamber body 1712 is coupled to a sealing ring 1713 to assist in sealing off the chamber around the agitation stage and its O-ring.

The SIS 130 further includes an aspirator 1720 to evacuate out aerosols and fluids from the test tube as waste. The SIS 130 further includes a tube holder 1722, and an agitation stage 1724, and a pair of guide rods 1726 mounted to a base 1721. The agitation stage 1724 has an O-ring seal 1726 to seal against the inside surface of the cylindrical wall of the chamber body (a pressure cylinder) 1712. As its name implies, the agitation stage 1724 can be rotated to agitate a test tube in the test tube holder 1722 and any sample fluid with its cells/particles in the test tube.

The DDU chamber 128 and the SIS 130 are in the same cavity containment chamber formed by a case 200 and doors 112, 113 of the system 100. The air in the cavity can be conditioned to a desired temperature and filtered to reduce contamination. One or more fans can force air through air filters and at least one electrical heating/air conditioning element can be used to maintain a desirable range of temperatures of the sample in the SIS 130 and the sorted cells/molecules in the DDU chamber 128. To avoid disturbing drops being collected, the input air flow comes into the shared cavity nearer the SIS 130. The DDU chamber 128 and SIS 130 are under negative pressure from a vacuum to additionally help prevent cells/molecules/gases from escaping out of the cell sorter into the ambient air of the environment.

Integrated Air Conditioning Subsystem

Figure 7A:
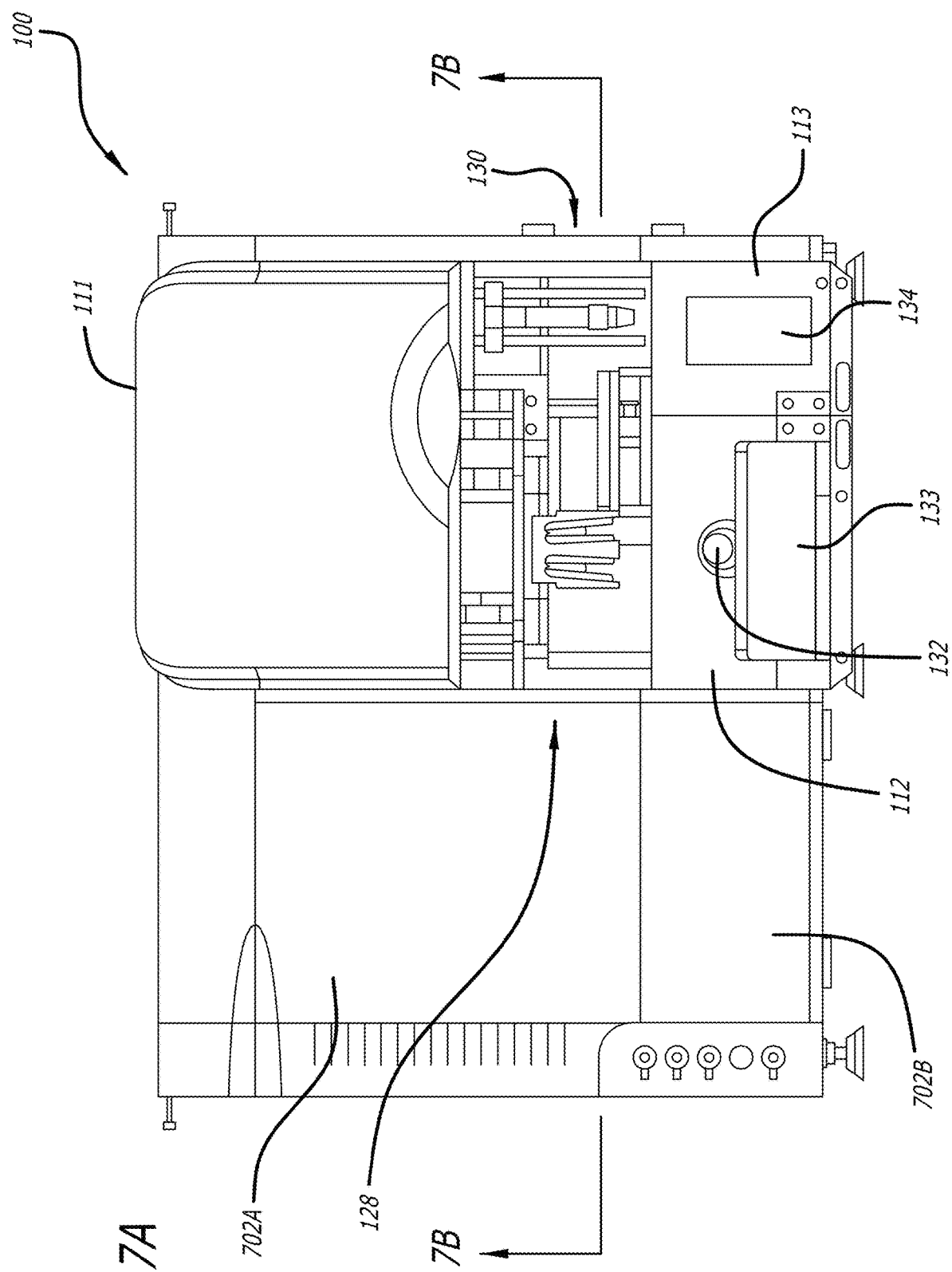
FIG. 7A is a front view of the of the compact cell sorter system indicating a general location of the droplet deflection unit (DDU) system.

FIG. 7A illustrates the sorting flow cytometer (cell sorter) 100 with the door 111 closed and the one or more panels 702A-702B mounted over the fluidics bucket 120. The doors 112-113 are pivoted open to see the DDU chamber 128 and a base of the deflection unit 122. The deflection unit selectively deflects drops of sample biological fluid, with the one or more biological cells or particles, from a center stream path 1699C into one or more left deflected stream paths and one or more right deflected stream paths about the center stream path 1699C. Drops passing out of the deflection unit 122 are to be collected in the DDU chamber 128. The DDU chamber 128 is in communication with the deflection unit 122 to receive the selected drops with the one or more biological cells or particles that are desired to be collected.

Figure 7B:
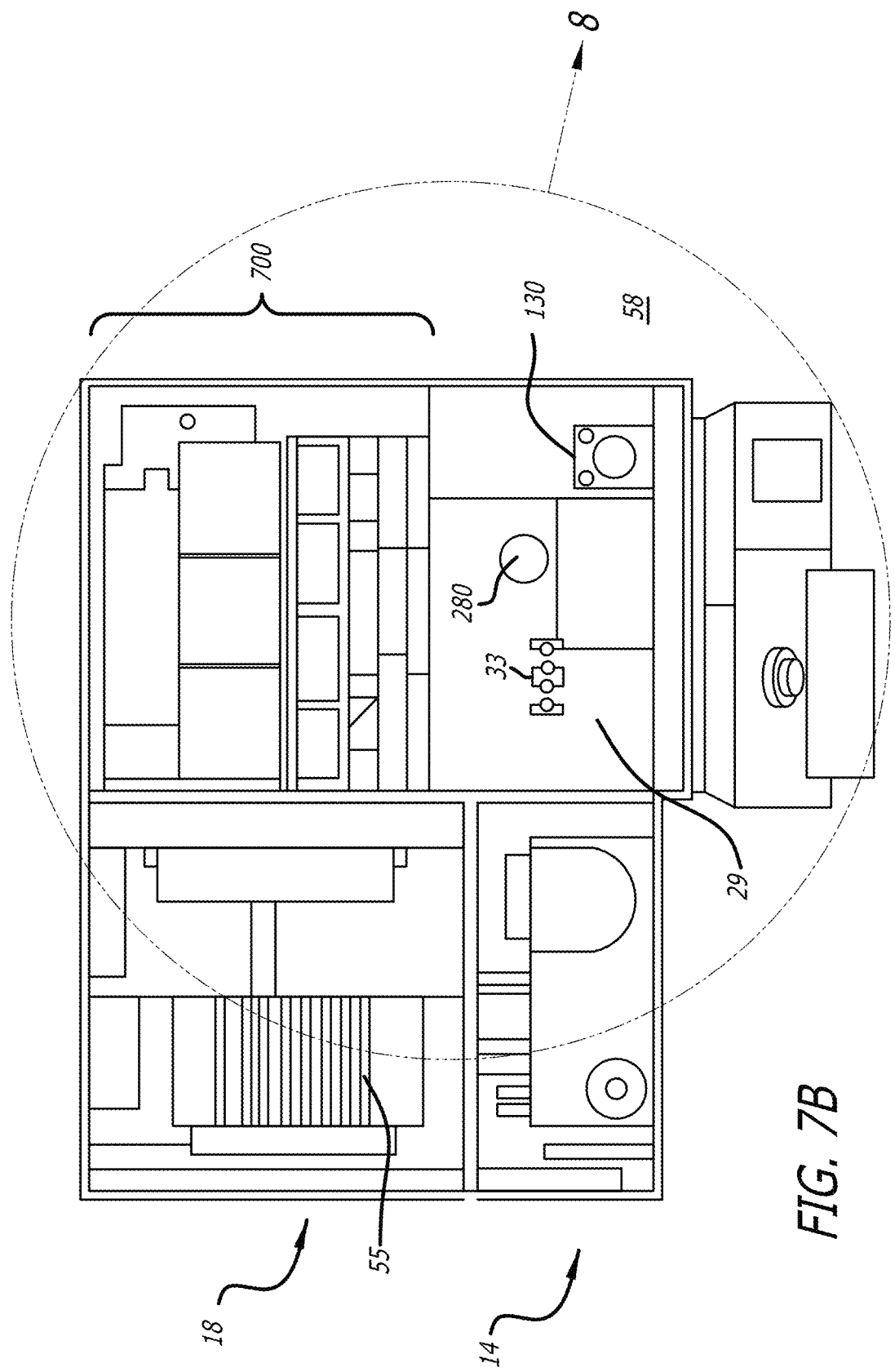
FIG. 7B is a cross sectional view of the of the compact cell sorter system showing the general location of the droplet deflection unit (DDU) subsystem in comparison with the electronics subsystem and the fluidics subsystem.

FIGS. 2A-2B illustrate front views of a portion of the cell sorter 100 with the doors 112-113 open revealing a case 200, a portion of the deflection unit 122, the drop deposition unit (DDU) (containment) chamber 128 and the sample input station (SIS) 130. FIG. 7B shows a cross sectional view of the cell sorter 100 illustrating various subsystems. The case 200 has an open face surrounded by edges of the case including a separation plate 206 at its base. The separation plate 206 forms the base of the DDU chamber 128 and is non-metallic to support the magnetic loading system disclosed in U.S. patent application No. 63/146,562, titled LOADING SYSTEM WITH MAGNETICALLY COUPLED SAMPLE MOVER FOR FLOW CYTOMETRY AND CELL SORTER SYSTEMS filed on Feb. 5, 2021. One or more hinges 202A-202B, 202C-202D are coupled to and between a bottom portion (base) of the case 200 and the doors 112-113 respectively. The doors pivot about the one or more hinges 202A-202B, 202C-202D.

When the doors are closed, the case 200 forms a portion of the containment chamber 128. The top side of the case has a top side opening aligned with base of the deflection chamber 122 to receive drops that were selectively deflected from the center stream 1699C of the sample biological fluid. The selected deflected drops are directed and loaded into one or more containers (e.g., test tubes or wells of a plate) in the containment chamber.

FIG. 2B illustrates a seal (top seal portion 212T, base seal 212B, side seal 212S, left side seal 212L, right side seal, and bottom seal 212B, collectively seal 212) that is mounted along edges of the case 200 of DDU chamber 128 and the sample input station 130. The seal 212 provides an air resistive seal when the DDU door 112 and sample door 113 are closed. The DDU door 112 has a shelf 133 (shown in FIG. 1C) that presses down on a top seal portion 212T when closed. Other portions of the seal 212, such as the bottom portion 212B and side portions 212S, 212L, are pushed on by the doors 112-113 and squeezed up against the edges of the DDU chamber 128. With the doors closed, the DDU chamber 128 and the SIS 130 are sealed off from the external ambient air of the environment (e.g., laboratory) where the cell sorter 100 is stationed. Furthermore, the DDU chamber 128 and SIS 130 are under negative pressure from a vacuum to additionally help prevent cells/molecules/gases from escaping out of the cell sorter into the ambient air of the environment, such as a laboratory.

To keep the doors 112-113 closed, the cell sorter/flow cytometer system 100 includes one or more electromagnetic locks. The electromagnetic locks comprise an electromagnet 203A-203B, 205A mounted to the case 200 and a metal catch 206A-206C coupled to an inside surface of the door 112, 113. When the door 112, 113 is closed, the electromagnet can be energized and attract the metal catch to it holding it closed so any harmful aerosols or particles are not released into the ambient air. Because the electromagnet requires power and is not always energized, at least one passive magnetic lock may also be used to hold the doors closed. The passive magnetic lock includes at least one magnet 205A-205C mounted to the case 200 and a metal catch coupled to the door. The door may be metallic, in which case, a portion of the door may provide the metal catch. In any case, the passive magnet 205A-205C attracts the metal catch and can keep the door 112, 113 closed even when power is no longer provided.

In FIG. 2A, the DDU chamber 128 of the cell sorter 100 is viewable with both the doors 112-113 pivoted to open positions. Openings in a wall 208 of the DDU chamber 128 show an input air filter 204I and an output air filter 204O mounted within tunnels leading into and out of an air conditioning chamber. Behind the wall 208 are one or more fans and at least one heating/air conditioning element to force the air through the air filters and maintain a desirable range of temperatures of the sample in the SIS 130 and the sorted cells/molecules in the chamber 128.

The DDU door 112 and sample input door 113, along with the seal 212, provide a good seal to isolate the DDU chamber 128 from other parts of the flow cytometer/cell sorter 100 as well as the ambient environment. The sample drops sorted out and captured in the DDU chamber 128 may desire a temperature-controlled environment to maintain them. Furthermore, the cells that are captured may be a pathogen that are not desired to be an aerosol and escape into the environment. Accordingly, with the magnetic loading system and the sealed doors, the cell sorter can provide an integrated filtration system and temperature-controlled environment to the DDU chamber 128. The DDU chamber may be referred to as the containment chamber 128 herein because it contains the aerosols while sorting occurs.

Referring now to FIG. 7A, a front view of the of the compact cell sorter system 100 generally indicates the droplet deflection unit (DDU) subsystem 58 and its containment chamber 128. FIG. 7B illustrates a cross sectional view of the compact cell sorter system 100 showing the general location of the droplet deflection unit (DDU) subsystem 58 comprising the sorting 33 and loading 29 subsystems shown in FIG. 1A in comparison with the electronics subsystem 18 and the fluidics subsystem 14. The droplet deflection unit (DDU) subsystem 58 can include an air conditioning subsystem 700 that maintains a temperature of the containment chamber and filters the aerosols.

Figure 8:
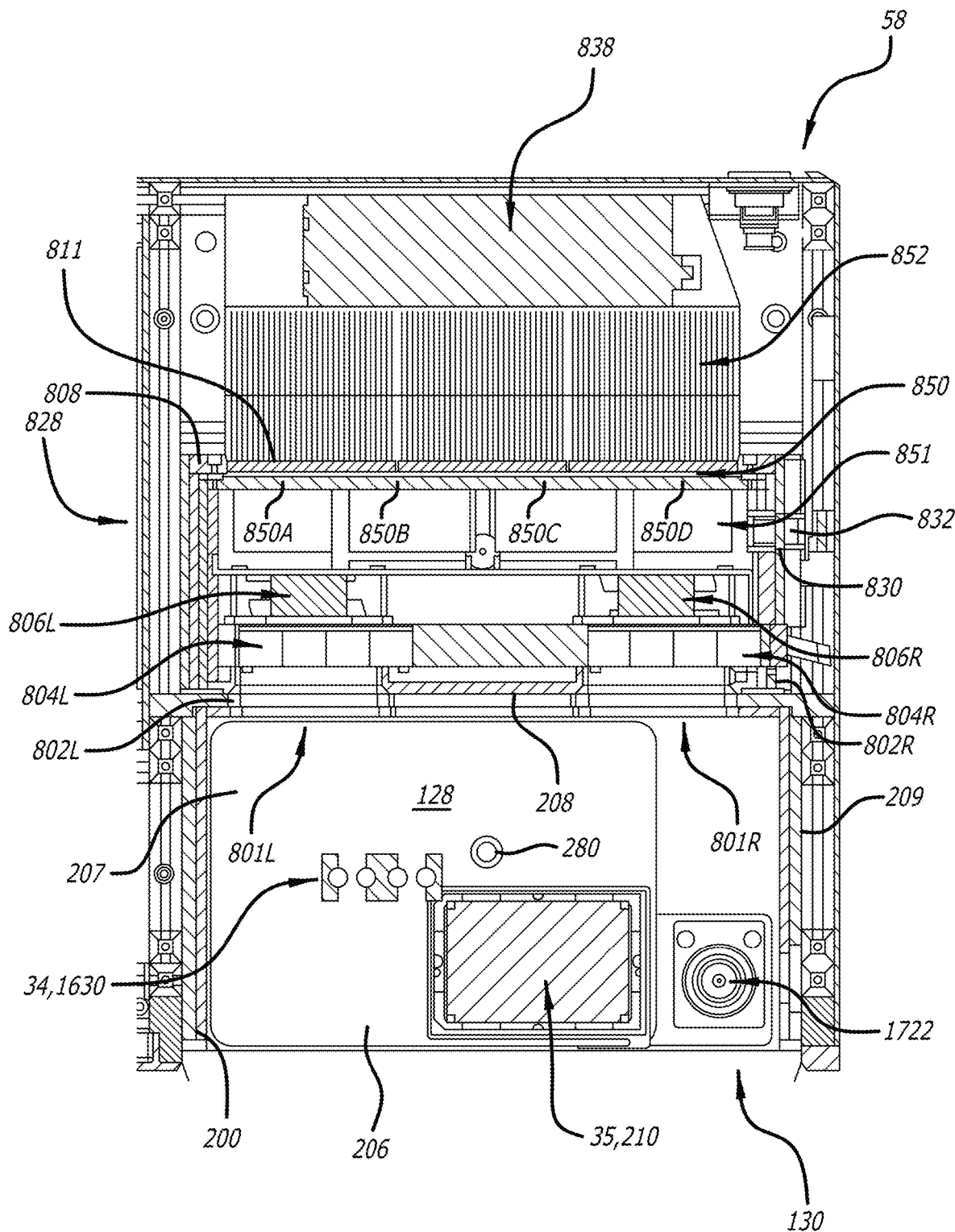
FIG. 8 is a magnified cross sectional view of the droplet deflection unit (DDU) subsystem in the compact cell sorter system.

FIG. 8 is a magnified cross sectional view of the droplet deflection unit (DDU) subsystem 58 in the compact cell sorter system. The droplet deflection unit (DDU) subsystem 58 includes the sorting 33 and deposition 29 subsystems as well as the air conditioning subsystem 700. The DDU chamber 128 includes the deposition subsystem 29 and the sample input station (SIS) subsystem 130 to support maintaining the sorted sample drops as well as the input sample in the sample tube that is located in the sample input holder 1722 shown in FIGS. 6B and 8.

The case 200 around the containment chamber 128 has a left side wall 207, a right side wall 209, and a middle wall 208 between the left and right side walls such as shown in FIGS. 2A-2B and 8. A top side 211 of the case 200 couples to the top edges of the left side wall 207, middle wall 208, and the right side wall 209. The bottom side or base of the case 200 in the containment chamber 128 is the separation plate 206. The separation plate 206 supports the magnetic deposition system. The base of the case 200 in the air conditioning chamber 828 can be formed of same material as the walls.

As shown in FIG. 8, the middle wall 208 has a left tunnel opening 801L near the left side wall of the case into a left tunnel 802L. The middle wall 208 further has a right tunnel opening 801R near the right side wall of the case into a right tunnel 802R. The left tunnel 802L and the right tunnel 802R are between the containment chamber 128 and an air conditioning chamber 828. The air conditioning chamber 828 is part of the air conditioning subsystem 700 for cooling or heating air as needed to control the temperature to a set temperature. The set temperature can be input by a user through a software user interface and controlled by software stored in memory and executed by a processor of a personal computer (PC) or computer workstation.

The air conditioning subsystem 700 can further include a left air filter 804L that is mounted in the left tunnel 802L and a right air filter 804R that is mounted in the right tunnel 802R. The air conditioning subsystem 700 further includes a left fan 806L aligned with the left air filter 804L and the left tunnel 802L and a right fan 806R aligned with the right air filter 804R and right tunnel 802R for moving air between the containment chamber and the air conditioning chamber through the filters. In some embodiments, the left air filter 804L and the right air filter 804R are high-efficiency particulate air (HEPA) filters. In some embodiments, the left air filter and the right air filters are ultra-low particulate air (ULPA) filters.

In the cell sorter system 100, the left tunnel 802L and left air filter 804L are nearer the drops dropping from the deflection unit than the right tunnel 802R and the right air filter 804R. The direction of air flow between the containment chamber and the air conditioning chamber is set up to try to avoid disturbing the drops as they drop into a well or a test tube from the deflection unit. Air flows out of the containment chamber 128 through the left tunnel 802L and left filter 804L into the air conditioning chamber 828 such as shown by arrows 902A-902B in FIGS. 9A-9B. Air flows into the containment chamber 128 through the right tunnel 802R and right filter 804R from the air conditioning chamber 828 such as shown by arrows 904A-904B in FIGS. 9A-9B. Accordingly, the left fan 806L pulls air from the containment chamber 128 through the left tunnel 802L and left filter 804L into the air conditioning chamber 828. The right fan 806R pushes air from the air conditioning chamber 828 through the right tunnel and right air filter 804R into the containment chamber 128. In this manner, the left filter and left fan can be referred to as the evacuation filter and evacuation fan while the right filter and right fan can be referred to as the return filter and the return fan. Of course, the sides in the containment chamber can be reversed (with deflection unit and test tubes/wells on the right and sample input on the left) and the air flow sides reversed.

The left air filter 804L removes cells/particles in the air flowing from the containment chamber 128 through the left tunnel 802L and into the air conditioning chamber 828. The right air filter 804R in the right tunnel 802R removes particles in the air flowing out from the air conditioning chamber 828 into the containment chamber 128. The left side fan 806L is aligned with the left tunnel 802L to pull air from the containment chamber 128 through the left air filter 804L and into the air conditioning chamber 128. The right fan 806R is aligned with the right tunnel 802R to push air from the air conditioning chamber 828 through the right air filter 804R and into the containment chamber 128.

As shown in FIG. 2A, selected sample drops are received from the deflection chamber 122 through a top side opening 250 in the case 200. The right fan 806R pushes air through the right air filter 804R, the right tunnel 802R, and into the containment chamber 128 in the side opposite the case where the top side opening 250 is located. Accordingly, the right fan 806R is positioned and its direction of pushing air into the containment chamber 128 is selected to avoid directly blowing air into the stream of drops being sorted out into containers (e.g., test tubes, wells of a plate). This is to avoid incorrectly capturing a particle or cell in the wrong container, such as an adjacent well of the plate than the one intended.

As shown in FIG. 8, the containment case 200 has a back wall 808 with an opening 811 that leads from the air conditioning chamber 828 into an open space 838 in the back of the system 100. The air conditioning subsystem 700 further includes a thermoelectric cooling (TEC) array 850 mounted in the back wall opening 811 of the case 200. The thermoelectric cooling (TEC) array 850 is mounted between the air conditioning chamber 828 and the open back space 838. The TEC array seals off the opening 811 in the back wall 808. The air conditioning subsystem 700 further includes a front side heat sink 851 coupled to a front side of the TEC array 850 and a back side heat sink 852 coupled to a back side of the TEC array 850.

The front side heat sink 851 extends out into the air conditioning chamber 828 from the TEC array 850 to heat or cool the air in the air conditioning chamber 828. The back side heat sink 852 extends out into the open space 838 form the TEC array 850 to sink heat into the ambient air or to absorb heat from the ambient air. In this manner the thermoelectric cooling (TEC) array 850 and back side heat sink can receive ambient air as a heat sink to cool down or as a cold sink to heat up the back side of the TEC array. The TEC array 850 has a plurality of TEC devices 850A-850D in a row to control the air temperature of the air in the air conditioning chamber 828 and the containment chamber 128.

The TEC array 850 is electrically coupled in the communication with a temperature control circuit 55 of the electronics subsystem 18 shown in FIGS. 1A,7B. A temperature sensor 280 is mounted in the containment chamber 128 to control the air temperature therein to maintain a desired temperature of the sample input and the sorted drops that are output by the cell sorter. In some embodiments, the temperature sensor is mounted in the containment chamber to the top side 211 of the case 200. The temperature sensor 280 is electrically coupled in the communication with the temperature control circuit 55 to provide feedback. The temperature sensor 280 samples the air temperature in the containment chamber 128 where the sample input is drawn and the selected drops are sorted out.

The control circuit 55 receives a desired air temperature setpoint from a software user interface and based on the sensed temperature, controls the TEC array 850 to heat and/or cool the air in the air conditioning chamber 828 that is then blown into the containment chamber 128 by the right side fan 806R. The TEC array can either heat up the air in the air conditioning chamber or cool down the air in the air condition chamber based on the current direction and level of control. The temperature control circuit 55 controls the TEC array 850 to heat the air in the air conditioning chamber 828 with a flow of current in a first direction over a range of amps. To warm the chamber 828, the front side of the TEC array is the warm side and the back side of the TEC array is the cool side. The temperature control circuit 55 controls the TEC array 850 to cool the air in the air conditioning chamber 828 with a flow of current in a second direction opposite the first direction over a range of amps. To cool the chamber 828, the front side of the TEC array is the cold side and the back side of the TEC array is the hot side. In either case, the cooled or warmed air in the air conditioning chamber 828 is pushed into the containment chamber 128 by the right fan 806R and pulled back into the air conditioning chamber 828 by the left fan 806L.

Figure 9A:
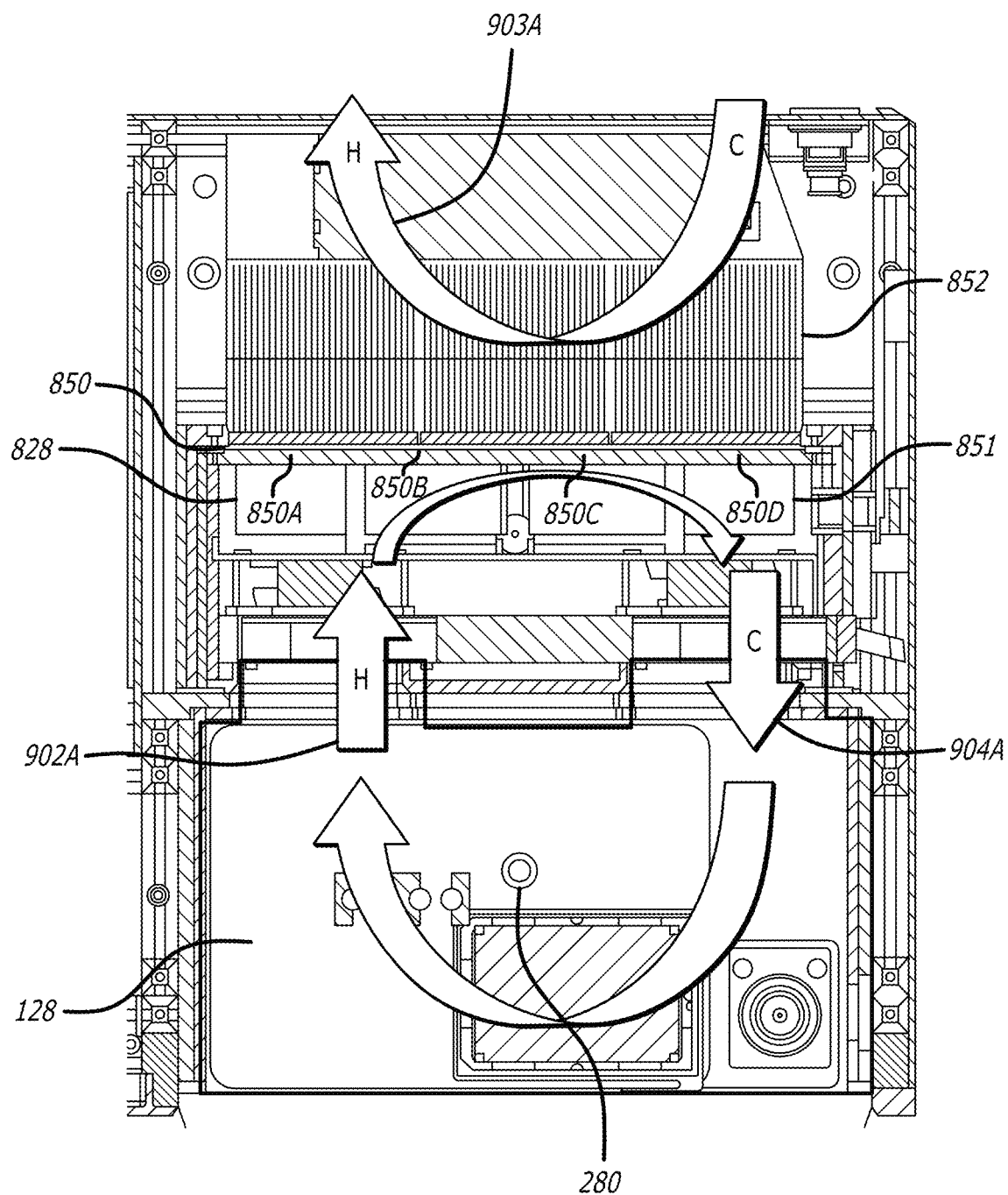
FIG. 9A is a magnified cross sectional view of the droplet deflection unit (DDU) subsystem in the compact cell sorter system in a normal mode illustrating normal cooling operation by the integrated heating and air conditioning subsystem.

Referring now to FIG. 9A, the temperature control circuit 55 controls the TEC array 850 to cool the air in the air conditioning chamber 828 with a flow of current in one direction. The front side of the TEC array 850 is the cold side and the back side of the TEC array is the hot side. The temperature control circuit 55 controls the TEC array 850 to cool the air in the air conditioning chamber 828. Heat in the air from the air conditioning chamber is drawn in by the front side heat sink 851 coupled to the front side of the TEC array making the air in the air conditioning chamber colder. Cool air from the air conditioning chamber 828 is pushed into the containment chamber 128 by the right side (return) fan 806R as indicated by the arrow head 904A. The cold air in the containment chamber 128 warms up from the objects therein including the sample and any sorted drops. The warm air is pulled from the containment chamber 128 by the left side fan as indicated arrowhead 902A.

The front side heat sink 851 draws cold from the front side of the TEC array and transferors it into the air in the air conditioning chamber 828. The back side heat sink 852 draws heat from the back side of the TEC array and transfers it into the ambient air as shown by arrowhead 903A with C being the cold side and H being the hot side with the direction of air flow over the back side heat sink. A fan in the open space 838 can be used to further the heat exchange process with the back side heat sink 852.

Figure 9B:
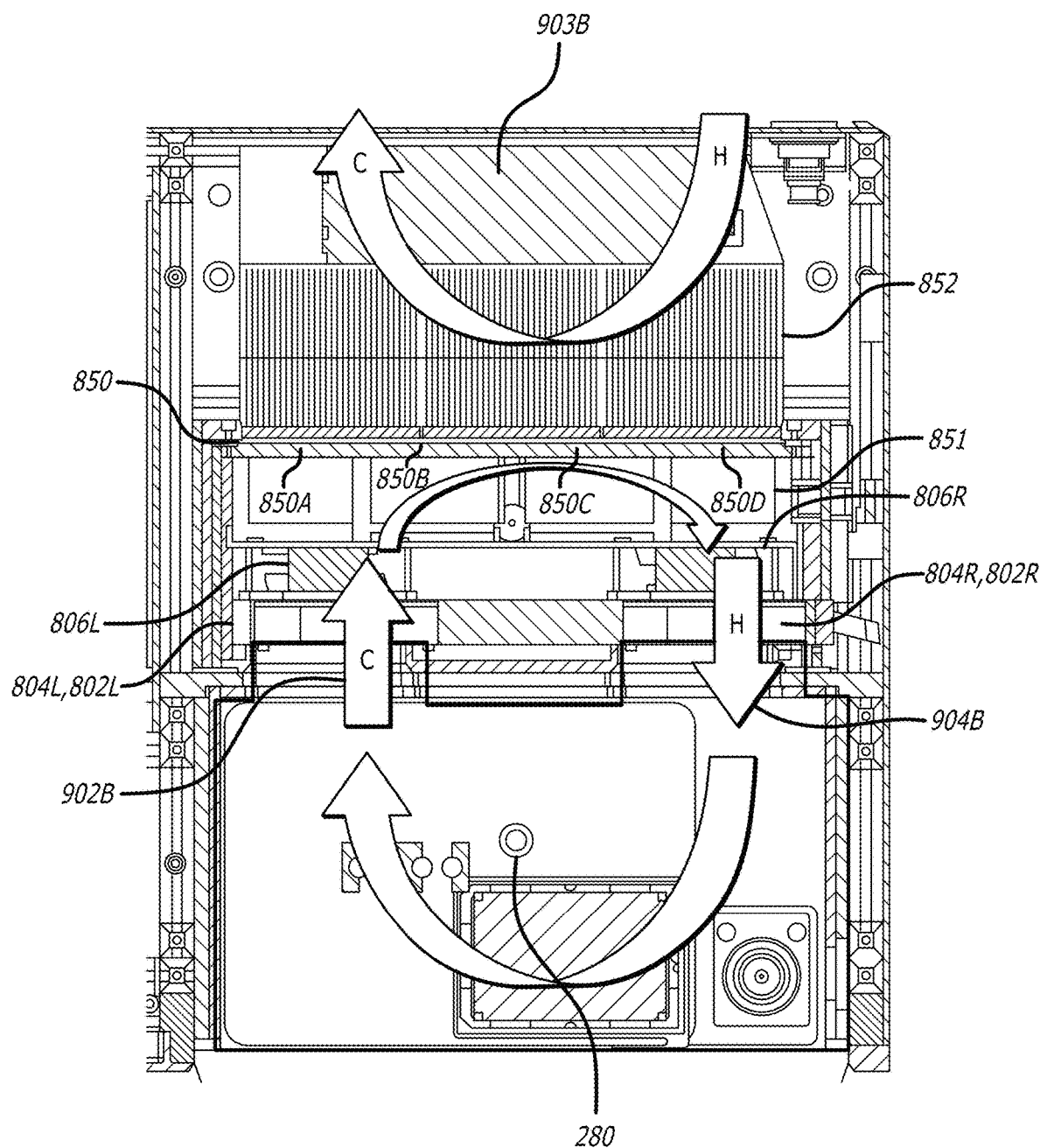
FIG. 9B is a magnified cross sectional view of the droplet deflection unit (DDU) subsystem in the compact cell sorter system in a normal mode illustrating normal heating operation by the integrated heating and air conditioning subsystem.

Referring now to FIG. 9B, the temperature control circuit 55 controls the TEC array 850 to heat the air in the air conditioning chamber 828 with a flow of current in another direction. The front side of the TEC array 850 is the hot side and the back side of the TEC array is the cold side. Heat from the front side of the TEC array is transferred into the front side heat sink 851 and into the air in the air conditioning chamber. Warm air from the air conditioning chamber 828 is pushed into the containment chamber 128 by the right side (return) fan 806R as indicated by the arrow head 904B with the letter H. The warm air in the containment chamber 128 transfers heat in to the objects therein including the sample and any sorted drops and cools down. Cold air is pulled from the containment chamber 128 by the left side fan as indicated arrowhead 902B with the letter C.

The front side heat sink 851 draws heat from the front side of the TEC array and transferors it into the air in the air conditioning chamber 828. The back side heat sink 852 draws heat from the ambient air and transfers it into the back side of the TEC array. After passing through the back side heat sink 852, the ambient air is colder as shown by arrowhead 903B with C being the cold side and H being the hot side with the direction of air flow over the back side heat sink. A fan can be used to further the heat exchange process between ambient air and the back side heat sink 852.

Figure 10A:
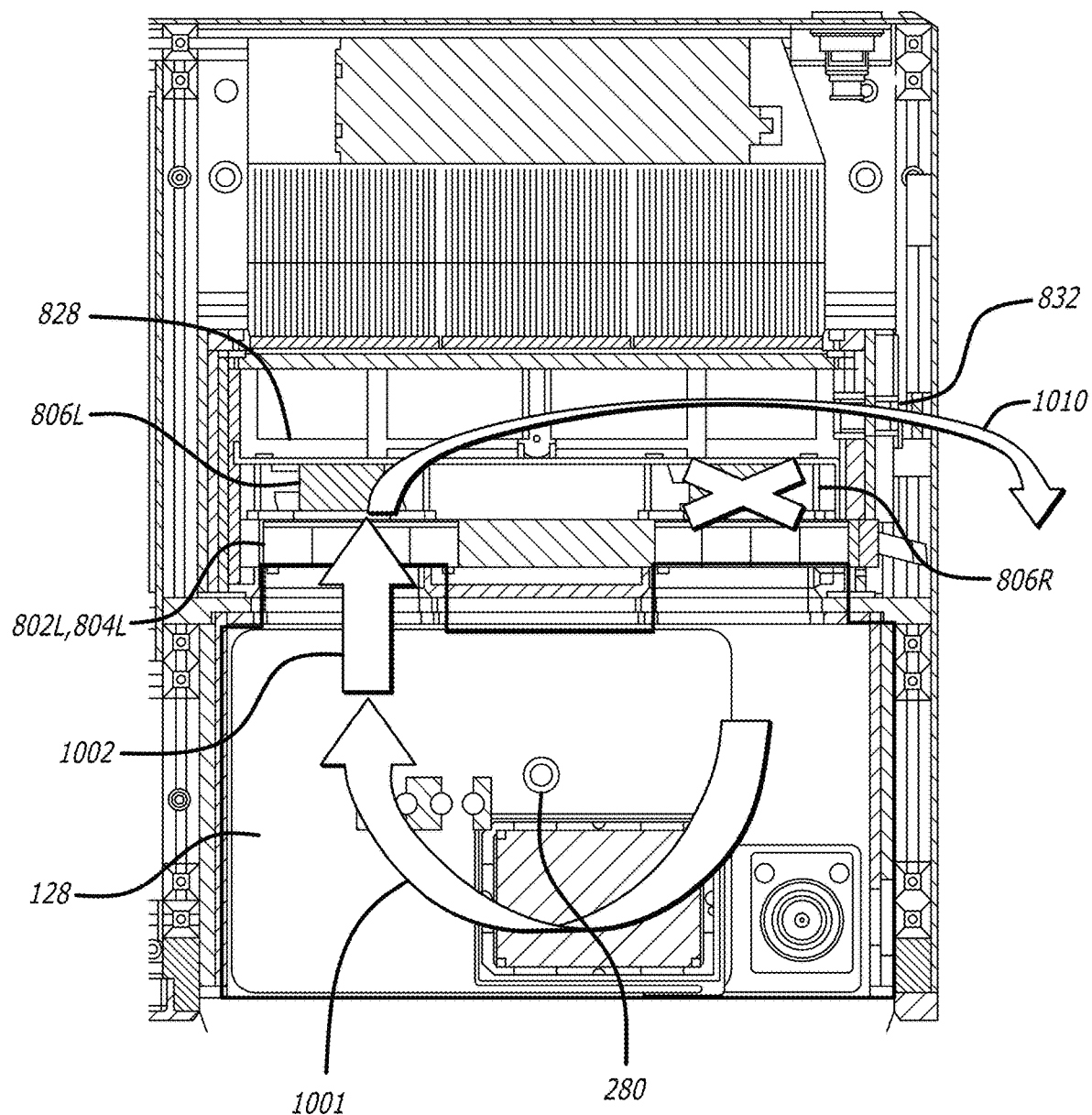
FIG. 10A is a magnified cross sectional view of the droplet deflection unit (DDU) subsystem illustrating an evacuation operation performed by the compact cell sorter system in an evacuation mode.
Figure 10B:
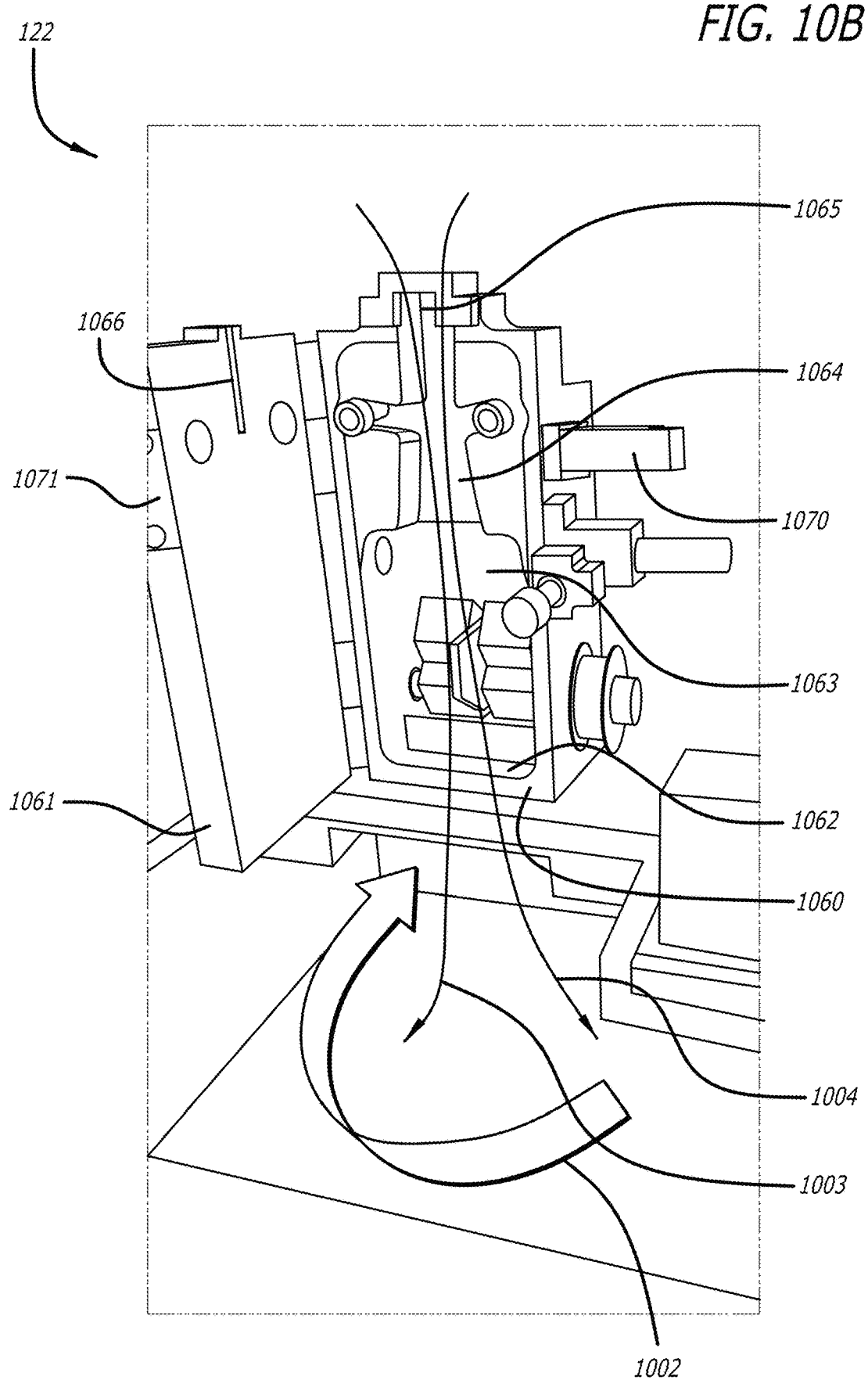
FIG. 10B is a front view of the deflection unit with door open illustrating air flow during the evacuation operation performed by the compact cell sorter system in an evacuation mode.

Referring now to FIGS. 8 and 10A-10B, when sorting is finished on a sample or an emergency occurs and it is desirable to open the doors 112, 113, evacuation of the air and aerosols in the chambers 128, 828 out through an evacuation vent 832 can occur. The air in the chambers of the deflection unit 122 can also be evacuated. Before allowing access to the samples, the magnetic locks can maintain the closure of the doors 112, 113 until the air in the chambers has been cycled for a predetermined period of time through the air filters between the chambers 128, 828 such as shown in FIGS. 9A-9B. The start of the predetermined period of time can be based on manual selection by a user through a mechanical button (abort/interrupt button) or a software button (abort/interrupt button) in a software user interface, at the end sample input and sorting by the cell sorter, or at the end of sample input and the running of the sample through the flow cytometer.

To support air evacuation out of the cell sorter system, the case 200 further has an evacuation opening 830 in a side wall of the air conditioning chamber 828. The evacuation vent 832 is mounted in the evacuation opening 830. The evacuation vent 832 is a valve that is selectively opened to vent air from the air conditioning chamber 828 out of the cell sorter/flow cytometer. The evacuation vent 832 can be passively operated with a flap valve that is opened/closed by air pressure. Alternatively, the evacuation vent can be active with a flap valve that is driven by a reversable motor to be opened/closed under software/hardware control.

As shown in FIG. 10A, to evacuate air through the evacuation vent, the left fan 806L remains turned on and the right fan 806R is shut off. The left fan 806L pulls air out of the containment chamber 128 (arrow heads 1002-1002) and out from the deflection unit 122 (see arrow heads 1003, 1004 in FIG. 10B) and into the air conditioning chamber 828. The air in the air conditioning chamber 828 is pushed out from the air conditioning chamber (see arrow head 1010 in FIG. 10A) and through the open valve of the evacuation vent 832 by the left fan 806L.

The air in the chambers can be vented through the vent 832 into the ambient air just outside the cell sorter/flow cytometer, such as a laboratory room or the ambient air in a specific laboratory confined space. Alternatively, an exhaust hose can be affixed outside the system around the evacuation vent so that the evacuated air from the chambers can be moved to a remote space away from the laboratory for further treatment.

The air in the containment chamber 128 of the cell sorter/flow cytometer system 100 can be evacuated into the air conditioning chamber 828 and out through the evacuation vent 832 shown in FIG. 10A. To do so, the return fan (right fan) aligned with the right tunnel, that ordinarily pushes air from the air conditioning chamber into the containment chamber, is turned off. If off, the evacuation fan (left fan) aligned with the left tunnel, that pulls are out of the containment chamber through the left tunnel into the air conditioning chamber, is turned on. If closed, the valve in the evacuation vent 832 is opened. Accordingly, with the valve open, the evacuation fan (left fan) can push the air in the air conditioning chamber out through the evacuation vent into the environment. The evacuation fan is continuously run for a predetermined period of time to evacuate air out of the containment chamber and the air conditioning chamber.

FIG. 10B shows the deflection unit 122 with its door 1061 open and swung away from the back body/case 1060 and the latch 1070 released from the catch 1071. As shown in FIG. 10B, the continuous running of the left (evacuation) fan 806L for the predetermined period of time can further evacuate air from the sorting chamber 1063 and the deflection chamber 1064 through the drop slot 1062 into the containment chamber 128, the air conditioning chamber 828 and out the evacuation vent 832. Additional air can be pulled for evacuation out through the evacuation vent from inside the cell sorter through the stream opening 1065 at the top of the deflection unit 122 as indicated by the arrows 1003, 1004. A channel 1066 in the door 1061 can assist in the evacuation of air from the cell sorter. After the predetermined period of time has elapsed, the evacuation fan 806L can be turned off and then the magnetic locks released so that the doors 112, 113 can be manually opened.

ADVANTAGES

There are a number of advantages to the cell sorter 100, its assemblies and sub-assemblies. The air conditioning of air around the samples is integrated into a compact unit so that it is readily available without having to attached external air hoses or an external heater or an external air conditioner. Horizontal adjustments are provided both manually with a knob and remotely under motor control so that the position of the center stream path 1699C of drops is appropriately positioned. The air in the containment chamber, and elsewhere in the system, can be automatically filtered, heated/cooled, and evacuated when needed.

This disclosure contemplates other embodiments or purposes. It will be appreciated that the embodiments of the invention can be practiced by other means than that of the described embodiments, which are presented in this description for purposes of illustration and not of limitation. The specification and drawings are not intended to limit the exclusionary scope of this patent document. It is noted that various equivalents for the particular embodiments discussed in this description may be practiced by the claimed invention as well. That is, while specific embodiments of the invention have been described, it is evident that many alternatives, modifications, permutations and variations will become apparent in light of the foregoing description. Accordingly, it is intended that the claimed invention embrace all such alternatives, modifications and variations as fall within the scope of the appended claims. The fact that a product, process, or method exhibits differences from one or more of the described exemplary embodiments does not mean that the product or process is outside the scope (literal scope and/or other legally-recognized scope) of the following claims.

What is claimed is:

1. A compact sorting flow cytometer system comprising:
    a flow cell to form a stream of a plurality of drops of a sample biological fluid with one or more biological cells or particles, the flow cell having a flow cell body with a port receiving a conductive hose fitting to receive a signal from a sort controller to selectively apply a charge to a sheath fluid and at least one drop of the sample biological fluid to form at least one charged drop and otherwise leave a plurality of uncharged drops;
    a deflection unit in communication with the flow cell to receive the at least one charged drop and the plurality of uncharged drops in the stream of the sample biological fluid, the deflection unit including:
        a case having a deflection cone and a deflection chamber in communication with the flow cell to receive the at least one charged drop and the plurality of uncharged drops in the stream, the case further having a tub with a drain in the deflection chamber to aspirate drops into a waste outlet, the case further having a slot at a base;
        a first electrostatic charge plate and a second electrostatic charge plate opposite the first electrostatic charge plate mounted in the deflection cone with a progressively larger gap between each, the first charge plate to receive a high positive voltage and the second charge plate to receive a high negative voltage to form an electrostatic charge field through which the at least one charged drop and the plurality of uncharged drops in the stream pass, wherein the plurality of uncharged drops pass through the electrostatic charge field in a center stream path of drops of the sample biological fluid and the at least one charged drop is deflected away from the center stream path; and
        a first pivotal scupper, a second pivotal scupper, and a non-pivotal center collector between the first pivotal scupper and the second pivotal scupper are arranged along a first shaft in the tub of the case, wherein the first pivotal scupper and the second pivotal scupper pivot with the first shaft between a first position to direct drops into the tub for aspiration down the drain and a second position to allow the at least one charged drop deflected away from the center stream path to pass through the slot for collection, wherein the non-pivotal center collector is non-pivotal to direct the plurality of uncharged drops in the center stream path into the tub for aspiration down the drain.

2. The compact sorting flow cytometer system of claim 1, wherein
    the first pivotal scupper, the second pivotal scupper, and the non-pivotal center collector are horizontally adjustable (side to side) with the first shaft to align the non-pivotal center collector with the center stream path of the plurality of uncharged drops from the flow cell.

3. The compact sorting flow cytometer system of claim 1, further comprising:
    a second shaft inserted through a hollow opening in the first shaft; and
    a threaded adjustment knob engaged with threads of the second shaft to pull on the second shaft as turned in one direction and push out on the second shaft as turned in the opposite direction to adjust the horizontal position of the first pivotal scupper, the second pivotal scupper, and the non-pivotal center collector.

4. The compact sorting flow cytometer system of claim 3, wherein
    the deflection unit is slidingly mounted to at least one rail and horizontally adjustable along the at least one rail to adjust a position of the center stream path.

5. The compact sorting flow cytometer system of claim 4, wherein
    the deflection unit is horizontally adjusted to adjust the position of the center stream path to be equidistant between the first electrostatic charge plate and the second electrostatic charge plate in the deflection cone.

6. The compact sorting flow cytometer system of claim 3, further comprising:
a first pulley coupled to the first shaft;
a reversible electric motor with a second pulley coupled to a third shaft, the third shaft rotated clockwise and counter clockwise by the reversible electric motor;
a continuous belt mounted over the first pulley and the second pulley;
wherein the continuous belt drives the first pulley in response to the reversable electric motor to pivot the first pivotal scupper and the second pivotal scupper pivot between the first position and the second position.

7. The compact sorting flow cytometer system of claim 1, wherein
the deflection unit is slidingly mounted to at least one rail and horizontally adjustable along the at least one rail to adjust a position of the center stream path.

8. The compact sorting flow cytometer system of claim 7, wherein
the deflection unit is horizontally adjusted to adjust the position of the center stream path to be equidistant between the first electrostatic charge plate and the second electrostatic charge plate in the deflection cone.

9. The compact sorting flow cytometer system of claim 1, wherein the signal is one of
a ground signal apply ground to the sheath fluid and leave the plurality of uncharged drops uncharged;
a positive charge signal to apply a positive charge to the sheath fluid that is transferred to a drop to form a positively charged drop; and
a negative charge signal to apply a negative charge to the sheath fluid that is transferred to a drop to form a negatively charged drop.

* * * * *